(12) United States Patent
Walt et al.

(10) Patent No.: US 6,285,807 B1
(45) Date of Patent: Sep. 4, 2001

(54) FIBER OPTIC SENSOR FOR LONG-TERM ANALYTE MEASUREMENTS IN FLUIDS

(75) Inventors: David R. Walt, Lexington; Mary Beth Tabacco, Boston, both of MA (US); Mahesh Uttamlal, Glasgow (GB)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/192,993

(22) Filed: Nov. 16, 1998

(51) Int. Cl.$^7$ ............................... G02B 6/00; G01N 21/64
(52) U.S. Cl. ................ 385/12; 250/227.14; 250/227.18; 436/172; 436/171
(58) Field of Search ..................................... 385/130, 123, 385/12, 129, 131; 250/227.21, 227.14, 227.18, 227.23; 436/172, 69, 171, 133

(56) References Cited

U.S. PATENT DOCUMENTS

| | | |
|---|---|---|
| 4,822,746 | 4/1989 | Walt . |
| 4,892,383 * | 1/1990 | Klainer et al. .................... 350/96.29 |
| 4,954,318 | 9/1990 | Yafuso et al. . |
| 5,059,790 * | 10/1991 | Klainer et al. .................. 250/227.21 |

(List continued on next page.)

FOREIGN PATENT DOCUMENTS 0 263 693    4/1988  (EP) .

OTHER PUBLICATIONS

U.S. application No. 08/851,203, Walt et al., filed May 5, 1997.
U.S. application No. 08/944,850, Walt et al., filed Oct. 6, 1997.
U.S. application No. 08/519,062, Walt et al., filed Aug. 24, 1995.
U.S. application No. 09/140,352, Walt et al., filed Aug. 26, 1998.

(List continued on next page.)

*Primary Examiner*—Frank G. Font
*Assistant Examiner*—Michael P. Mooney
(74) *Attorney, Agent, or Firm*—Bromberg & Sunstein LLP

(57) ABSTRACT

A robust fiber optic sensor and sensing method for reliable, long-term measurement of analytes is disclosed. The sensor comprises an optical interrogation region comprising an indicator dye confined at a distal end of an optical fiber and an analyte permeable membrane enclosing the interrogation region at the distal fiber end. In a preferred embodiment, a reservoir member is provided with excess dye for continuous replenishment of the interrogation region with dye over the lifetime of the sensor. In another preferred embodiment, the reservoir member comprises an indicator support for containment of excess dye. In one preferred embodiment, a ratiometric dye is used for monitoring optical signal-to-noise and signal drift caused by sensor aging. The sensor may be configured with a variety of alternative indicator dyes and membrane materials as a specific ion sensor for analyzing dissolved analytes such as gases, cations, and anions. The sensor may be configured for a wide dynamic detection range and sensitivity for specific analytes. In one embodiment, a $CO_2$ is disclosed which has a reversible working dynamic detection range between 200 and 1000 ppm $pCO_2$ and a sensitivity ±1 ppm. An integrated measurement system and measurement methods for remote sensing applications are also disclosed which comprise electro-optic and data acquisition modules coupled to a conventional satellite transmission system. The sensor and sensing methods of the present invention have utility in remote sensing of analytes for environmental, industrial, chemical, biochemical, and biological monitoring of gases and liquids.

14 Claims, 14 Drawing Sheets

U.S. PATENT DOCUMENTS

| | | | |
|---|---|---|---|
| 5,094,958 | * | 3/1992 | Klainer et al. .................. 436/172 |
| 5,114,864 | * | 5/1992 | Walt .................................. 436/528 |
| 5,143,853 | | 9/1992 | Walt . |
| 5,244,636 | | 9/1993 | Walt et al. . |
| 5,244,813 | * | 9/1993 | Walt et al. ..................... 436/172 |
| 5,250,264 | | 10/1993 | Walt et al. . |
| 5,252,494 | | 10/1993 | Walt . |
| 5,254,477 | | 10/1993 | Walt . |
| 5,258,616 | * | 11/1993 | Gutcheck et al. ............ 250/227.21 |
| 5,298,741 | | 3/1994 | Walt et al. . |
| 5,320,814 | | 6/1994 | Walt et al. . |
| 5,512,490 | | 4/1996 | Walt et al. . |
| 5,633,972 | | 5/1997 | Walt et al. . |
| 5,714,121 | | 2/1998 | Alderete et al. . |
| 5,814,524 | | 9/1998 | Walt et al. . |
| 5,832,165 | * | 11/1998 | Reichert et al. ................ 385/130 |
| 5,882,936 | * | 3/1999 | Bentsen et al. .................. 436/68 |
| 5,910,448 | * | 6/1999 | Atwater et al. ................. 436/133 |
| 5,919,712 | * | 7/1999 | Herron et al. .................. 436/518 |
| 5,961,924 | * | 10/1999 | Reichert et al. ............... 422/82.11 |
| 6,023,540 | * | 2/2000 | Walt et al. ...................... 385/12 |

OTHER PUBLICATIONS

U.S. application No. 09/033,462, Walt et al., filed Mar. 2, 1998.

U.S. application No. 09/151,877, Walt et al., filed Sep. 11, 1998.

U.S. application No. 09/187,289, Walt et al., filed Nov. 5, 1998.

C. Munkholm, et al., "A Fiber–Optic Sensor for CO2 Measurement ", Talanta, vol. 35, No. 2, pp. 109–112, 1988.

S. Barnard, et al., "A fibre–optic chemical sensor with discrete sensing sites", Nature, vol. 353, pp. 338–340, Sep. 26, 1991.

M. Uttamlal, et al., "A Fiber–Optic Carbon Dioxide Sensor for Fermentation Monitoring", Bitechnology, vol. 13, pp. 597–601, Jun. 1995.

P. Pantano, et al., "Analytical Applications of Optical Imaging Fibers", Report, Analytical Chemistry, Optical Imaging Fibers 481A, Aug. 1, 1995.

Z. Zhujun, et al., "A Carbon Dioxide sensor Based on Fluorescence", Analytica Chimica Acta, 160: 305–309 (1984).

Y. Kawabata, et al., "Fiber–Optic for Carbon Dioxide with a pH Indicator Dispersed in a Poly (Ethylene Glycol) Membrane", Analytica Chimica Acta, 219:223–229 (1989).

B. Weigl, et al., "Chemically and mechanically resistant carbon dioxide optrode based on a covalently immobilized pH indicator", Analytica Chimica Acta, 282:335–343 (1993).

A. Mills, et al., "Fluorescence Plastic Thin–film Sensor for Carbon Dioxide", Analyst, vol. 118, pp. 839–843, Jul. 1993.

D. Walt, et al., "Multiple–indicator fiber–optic sensor for high–resolution pCO2 sea water measurements", Analytica Chimica Acta, 274:47–52 (1993).

M. DeGrandpre, et al., "Simultaneous mooring–based measurements of seawater CO2 and O2 off Cape Hateras, North Carolina", Limnol. Oceanogr. 42(1): 21–28 (1997).

* cited by examiner

FIBER OPTIC SENSOR FOR LONG-TERM ANALYTE MEASUREMENTS IN FLUIDS

FIELD OF THE INVENTION

The present invention is generally concerned with chemical sensors, sensing apparatus, and sensing methods for the detection of analytes in fluids and is particularly directed to the design, construction and use of a robust, stable, low maintenance, fiber optic chemical sensor capable of long-term detection of a diversity of analytes with high sensitivity over a broad composition range.

BACKGROUND OF THE INVENTION

The monitoring of analytes in gases and liquids have numerous applications in industrial chemical processes, bioprocessing, fermentation processes, and environmental monitoring of the atmosphere, oceans, lakes, streams and groundwater. Typically, such processes are fairly complex and comprise a number of chemical or biochemical species of interest which are either indicative of performance, beneficial to the process or potentially harmful to the viability of such processes.

It is well known, for example, that bioprocess or fermentation process performance may be evaluated by the production or disappearance of key analytes and measurement of pH, dissolved oxygen, carbon dioxide and glucose. Industrial process performance may be assessed by monitoring of oxygen, carbon dioxide, nitrogen oxides, sulfur oxides, cations such as alkali metals or metals, and anions, such as halides or anion salts. Both indoor and outdoor monitoring of oxygen, carbon dioxide, pH, nitrogen oxides, sulfur oxides, halogens, organic toxins, trace metals and heavy metals are frequent required in assessments of health and safety as well as environmental quality.

Such complex processes typically require continuous monitoring of analytes due to their dynamic nature. Conventional laboratory methods for continuous analysis of process analytes are typically cumbersome and costly, requiring in-situ sampling and off-site analysis which comprise complex separation of analytes from their sample matrix medium. Such sampling methods lack continuity for interfacing with such dynamic processes and preclude immediate feedback of analyte information for real-time process control. Thus, there is a need for cost-effective, real-time, in-situ, dynamic monitoring of such processes over extended time periods of operation.

Over the past decade, fiber optic chemical sensors have extended analytical chemistry capabilities for low cost, real-time, in-situ analysis of analytes in industrial, biological and environmental processes by eliminating the need for intermittent sampling and off-line analysis. Such sensors typically provide for analytes to be detected in their native sample medium without cumbersome separations and tedious sample preparation. These sensors operate by detecting optical changes of a sensing material or indicator dye on interaction with an analyte. Due to the variety of analyte-specific indicators available, such sensors may be used for monitoring a large number of analytes. Arrays of such sensors may be employed with either selective and semi-selective indicators for monitoring a large number of target analytes simultaneously. Due to the small size of the optical fibers employed in such sensors, typically ranging from sub-micron to 500 um in diameter, these sensors may be easily and unobtrusively accommodated in virtually any process or environmental sensing application.

The accurate monitoring of low level $pCO_2$ (0 to 1000 ppm) is important in many systems. For example, $CO_2$ is used as an aerial fertilizer in greenhouses; $CO_2$ enrichment from ambient levels (345 ppm) to 1000 ppm can improve tomato yield by 35% [Hand, D. *Grower.* 1985, 104 (3), 31]. Similarly, the production or disappearance of $CO_2$ is a key parameter in assessing the performance of various fermentation and bioreactor processes m the biotechnology industries. Therefore, robust sensing technology for the fast and accurate determination of low level $CO_2$ is highly desirable.

The measurement of low level $pCO_2$ is particularly important for environmental monitoring. Both oceanographic and fresh water measurements are important to understand global changes in the environment brought about by the burning of fossil fuels and the destruction of rain forests [Sarmiento, J. L. *C&E News.* 1993, 30]. Wide-reaching, long term monitoring of $pCO_2$ is a critical requirement for realistic and predictive modeling of ocean-atmosphere coupling and the balancing of the global $CO_2$ budget [Siindquist, E. T., *Science*, 1993, 259, 934]. At present, oceanographic $pCO_2$ seawater measurements are obtained by research ships using water sampling techniques. Such an approach is expensive and provides low spatiotemporal resolution due to the limited numbers of samples, which can be taken. Thus, there is an immediate need for inexpensive, low-level, high spatiotemporal resolution $pCO_2$ sensors which can be remotely deployed over large areas for continuous, long-term environmental monitoring.

With conventional methods, $CO_2$ in the gas phase is usually determined using IR measurements. However, dissolved $CO_2$ is typically measured by either electrochemical or colorimetric methods, techniques which are not suitable for continuous, long-term, remote, environmental monitoring. Particularly useful alternative methods for environmental monitoring of dissolved $CO_2$ utilize chemical sensors.

Most chemical sensors for dissolved $CO_2$, including the innovative sensor described herein, are based on the principles behind the Severinghaus electrode [Severinghaus, J. W., Bradley, A. F., *J2 Appi. Physiol.* 1956, 13, 515]. This electrochemical sensor consists of a pH electrode in contact with a bicarbonate buffer solution which is confined at the electrode surface by a gas permeable membrane, such as PTFE or silicone rubber. Certain features of the Severinghaus $CO_2$ electrode design have been incorporated in optical $CO_2$ sensor designs. With these optical sensor embodiments, the Severinghaus pH electrode is replaced with an absorbance or fluorescence-based pH sensitive indicator coupled to an optical fiber. With either optical or electrochemical sensor designs, the sensor measures the pH of the $HCO_3$ solution which is in equilibrium with $CO_2$ outside the membrane according to the following mechanism:

$$CO_2 \xleftrightarrow{membrane} CO_2 + H_2O \xleftrightarrow{K} H_2CO_3 \xleftrightarrow{K_n} HCO_3^- + H^+ \xleftrightarrow{K_2} CO_3^{2-} + 2H^+$$

The external $CO_2$ concentration is related to the internal $H^+$ concentration by the following equation [Jensen, M. A., Rechnitz, G. A. *Anal. Chem.* 1979, *SI*, 515]:

$$h^3 + nh^2 - (K_1 a_T + K_W)h - 2K_1 K_2 a_T = 0 \quad [1]$$

where n is the concentration of sodium ions in the internal solution, $h = [H^+]$, $K_W = h[OH^-]$, $a_T$ is the total analytical concentration of carbon dioxide in the indicator solution layer, $K_1=KK_a=hb/a$ and $K_2=hc/b$ where $b=[HCO_3^-]$ and $c=[CO_3^{2-}]$.

Fiber optic $CO_2$ sensors are known in the art for high-level dissolved $CO_2$ measurement. Both absorbance-based sensor designs [Vurek, G. G., Peterson, J. I., Goldstein, S. R. Severinghaus, J. W., *Fed. Proc. Am. Soc. Exp. Biol.* 1982, 41, 1484; Mills, A., Chang, Q., McMurray, N. *Anal. Chem.* 64, 64, 1383] and fluorescence-based sensor designs [Munkholm, C. and Walt, D. R., *Talanta,* 1988, 35, 109; Uttamlal, M., Walt, D. R., *Bio/Technology,* 1995, 13, 597; Mills, A., Chang, Q. *Analyst,* 1993, 118, 839; Zhujun, Z., Seitz., W. R. *Anal. Chim. Acia.* 1984, 160, 305] have been disclosed. However, most of these sensors are suitable only for high $CO_2$ levels (0.01–1 atm.) and only a few report ppm range sensitivity. While modifications which improve the sensitivity of these conventional fiber optic sensor designs have been disclosed, for example by employing inner filter effects to enhance sensitivity [Walt, D. R, Gabor, G., Goyet, C. *Anal. Chim. Actca* 1993, 274, 47], such modifications have been limited to improvements in maximum resolution of ±7 ppm.

In an alternative approach to modification of conventional fiber optic $CO_2$ sensors for improved sensitivity, DeGrandpre [DeGrandpre, M. D., *Anal. Chem.* 1993, 65 (4), 331] has disclosed a sensor that, unlike conventional fixed reagent fiber optic sensors, operates by the constant replacement of the sensing solution at the distal end of the fiber by employing a fluid pumping system. This sensor has improved sensitivity over conventional designs, operating in the 0–1000 ppm $CO_2$ range with an accuracy of ±0.8 ppm. While this sensor design is suitable for low-level $pCO_2$ measurents, it requires a somewhat cumbersome pumping system for replenishment of sensing solution which adds complexity, required maintenance, and increased sensor costs.

Thus, there is a pressing need for a simple, low cost, low maintenance, reliable and sensitive chemical sensor and sensing method for remote sensing of low-level, dissolved analytes for applications involving the environmental, industrial, chemical, biochemical, and biological monitoring of fluids.

SUMMARY OF THE INVENTION

The sensor and sensing method of the present invention offer a number of distinctive and innovative features which overcome the limitations of both conventional analytical devices and fiber optic chemical sensors for low-level, long-term, remote monitoring of dissolved analytes in environmental, industrial, chemical, biochemical, and biological fluids of interest. The sensor of the present invention provides for a robust, fiber optic chemical sensor for remote, long-term monitoring of a variety of dissolved analytes over a wide analyte concentration range, including ppm levels. The sensor of the present invention is capable of continuous and reliable monitoring of environmental, industrial, chemical, biochemical and biological fluids, liquids or vapors, in-situ for extended duration without replacement, user intervention, or maintenance.

The fiber optic sensor of the present invention comprises an optical fiber, an optical interrogation zone disposed at a distal fiber end, said interrogation zone comprising a sensor sample fluid comprising an analyte and an indicator dye for detection of the analyte, said interrogation zone being optically coupled to and in optical communication with said fiber, said zone being illuminated by excitation light conveyed through said fiber to said distal fiber end, the dimensions of said zone being defined by said illumination, and an indicator dye reservoir which is optically isolated from said interrogation zone, said reservoir comprising a dye fluid comprising a solution of excess indicator dye, said dye in said reservoir being in fluid contact with a sensor sample fluid in said optical interrogation zone so as to both provide for fluid transport of dye between said dye reservoir and said optical interrogation zone and to enable equilibration of the dye fluid in the reservoir with the sample fluid in the interrogation zone.

The sensor of the present invention may further comprise either a gas-permeable membrane or an analyte-permeable membrane covering said optical interrogation zone and said reservoir, said membrane disposed between a portion of the distal end of said fiber and an ambient fluid medium, which membrane allows a target analyte to diffuse from the ambient fluid medium into the optical interrogation zone for detection and restricts transport and loss of the indicator dye from the sensor to the ambient fluid. In one embodiment, the permeable membrane is either selective or semi-selective to the target analyte and restricts transport of interfering analytes from the ambient fluid into the sensor which would other wise compromise detection of the target analyte in the optical interrogation zone.

A key innovative feature of the sensor of the present invention is in providing an optically isolated reservoir of excess dye to replenish indicator dye in the optical interrogation region, where the optically interrogated dye in the interrogation region is rendered inactive over time due to photobleaching of the dye caused by repetitive exposure of the dye to excitation light in the optical interrogation region during optical measurements. By providing for continuous replenishment of inactive, photobleached indicator dye with active dye from the dye reservoir, inactive dye in the interrogation region is replaced with active dye and both the sensor lifetime and sensitivity are extended and enhanced by continuously offsetting any signal loss due to photobleaching and loss of active dye. The design further provides for the rapid equilibration of the dye fluid in the reservoir with the sample fluid in the interrogation zone and avoids signal drift or sensor instability due to any lag or delay in equilibration of pH, ionic strength, or dye concentration when spent dye in the interrogation zone is replenished by dye from the reservoir. This innovative design further provides for enhancing sensor detection limits due to the improved signal-to-noise ratio maintained over the lifetime of the sensor.

In one embodiment of the sensor of the present invention, the dye reservoir comprises a surplus dye solution confined in a chamber which is in fluid contact with the sample fluid in the interrogation zone. In one preferred embodiment, the dye reservoir further comprises a dye support member which holds excess dye fluid within the reservoir. In a preferred embodiment, the dye support member comprises a permeable polymer material which allows transport of fluid between the dye reservoir and interrogation zone and facilitates equilibration of both pH and ionic strength of the dye fluid and the sample fluid in the interrogation zone. In another preferred embodiment, the dye reservoir region comprises both a dye indicator solution confined in a fluid chamber and a dye support member which holds excess dye indicator. In one preferred embodiment, a ratiometric dye is employed as the indicator dye and measurements are made at two wavelengths. In this embodiment, the ratio of light intensities at the two wavelengths are used to monitor and offset the effect of photobleaching during the extended lifetime of the sensor.

In yet another embodiment, the sensor of the present invention provides for low-level, 0 to 1000 ppm, detection of dissolved analytes in fluids by providing for increased optical response and detection sensitivity of the sensor to trace levels of analytes. In this embodiment, a large diameter optical fiber is employed to increase the optical interrogation area and optical interrrogation zone of the sample. Additionally, for sensor embodiments capable of low-level analyte detection, fluorescent dye indicators are employed which provide a relatively strong emission intensity for low analyte levels. With these embodiments, sensitive, low-level photo detectors may also be employed for detection of low levels of emitted light.

In an additional aspect, the present invention provides method of making a robust, fiber optic chemical sensor for remote, long-term monitoring of a variety of dissolved analytes or a wide range of compositions. The method comprises providing an optical fiber with both an optical interrogation zone and a dye reservoir at a distal end of the fiber such that the optical interrogation zone is optically coupled to and in optical communication with the fiber and the dye reservoir is optically isolated from but in fluid contact with said optical interrogation zone.

In a further aspect, the present invention provides a method for remote sensing, detection and monitoring of target analytes in fluids, including both liquids or vapors. The method comprises providing a robust, fiber optic chemical sensor, as described herein, and contacting a sensing end of the sensor with a sample fluid. The concentration of dissolved analyte is determined by optically interrogating a sample fluid, comprising an analyte and indicator, in the interrogation zone with excitation light and detecting light emitted from the sample fluid due to the presence a target analyte.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

This invention is pointed out with particularity in the appended claims. Other features and benefits of the invention can be more clearly understood with reference to the specification and the accompanying drawings in which:

FIG. 4a shows the overall sensor housing design.

FIG. 4b shows details of the optical interrogation region and dye reservoir.

FIGS. 4c and 4d show schematics of a sensor cross-section;

Figure 1:
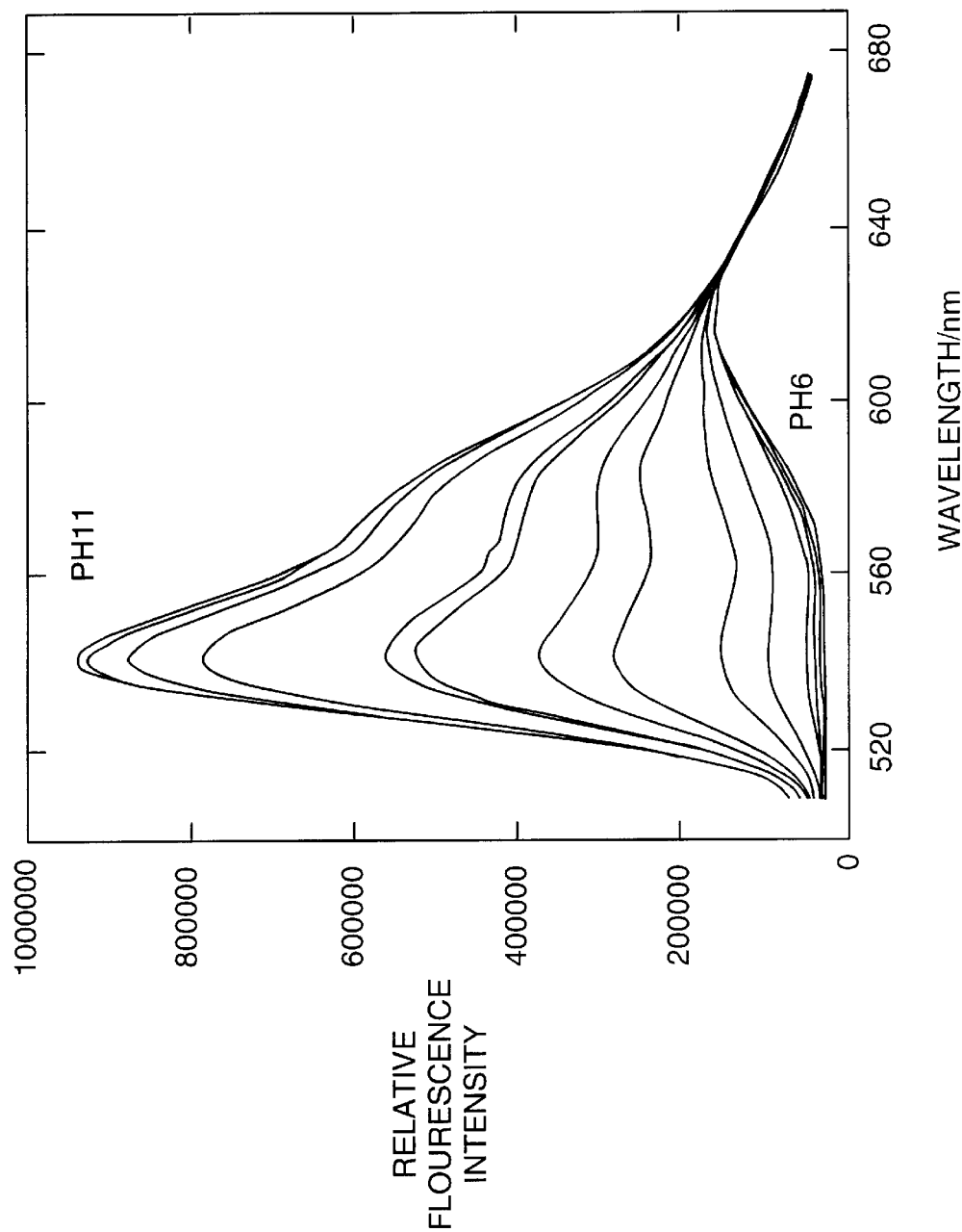
FIG. 1 shows an emission spectra of carboxy-SNAFL-1 at various pH values in distilled water when subjected to excitation at 488 nm. This plot shows measurements ranging from pH 6 to 11 using pH values shown in FIG. 2.

LIST OF SYMBOLS a $[CO_2]_{aq}$ (mol $dm^3$)

$a_T$ $[CO_2]_{aq}$+$[H_2CO_3]$ in the indicator solution layer

B background fluorescence intensity b $[HCO_3^-]$ (mol $dm^3$)

c $[CO_3^{2-}]$ (mol $dm^3$)

d [In] unprotonated dye concentration dh [HIn] protonated dye concentration $dh_T$ total dye concentration D diffusion coefficient of $CO_2$ through the membrane h $[H^+]$ (mol $dm^3$)

$\Delta H°_{buffer}$ dissociation enthalpy for the buffer under standard conditions $\Delta H°_{in}$ dissociation enthalpy for the indicator under standard conditions I fluorescence intensity of protonated form of the indicator dye or $I_{545}/I_{625}$ $I_x$ fluorescence intensity at wavelength x $I_o$ maximum fluorescence intensity (ratio)

$I_A$ fluorescence intensity of the acid form of the indicator dye $I_B$ fluorescence intensity of the base form of the indicator dye K equilibrium constant for $CO_2/H_2CO_3$ system $K_a$ first acid dissociation constant for carbonic acid $K_1$ =$K \cdot K_a$ $K_2$ second acid dissociation constant for carbonic acid $K_W$ dissociation constant for water $K_{in}$ acid dissociation constant for the indicator $K_M$ membrane constant n sodium ion concentration in the indicator solution $pH_o$ pH of indicator solution when $[CO_2]$=0

DETAILED DESCRIPTION OF THE INVENTION

The present invention is directed to a fiber optic chemical sensor comprising at least one optical fiber, an optical interrogation zone at a distal end of said fiber, which zone is optically coupled to and in optical communication with the fiber, a indicator dye reservoir which is optically isolated from the interrogation zone but in fluid contact with said zone, and an analyte permeable membrane which covers a surface of the sensor and provides for containment of a sample fluid within the interrogation zone of the sensor.

The optical interrogation zone of the sensor is primarily defined by the region, or interrogated sample volume, within the sensor which is illuminated by excitation light transmitted through the fiber to the zone during an optical measurement. The diametric dimension of the interrogation zone is approximately defined by the numerical aperture of the fiber with some slight variation due to divergence of the excitation light when emerging from the end of the fiber.

The interrogated sample volume which fills the interrogation zone volume within the sensor is typically comprised of a target analyte and an indicator dye which is responsive to the analyte and emits a characteristic optical signal upon illumination with excitation light. In one embodiment, the sample solution may further comprise a buffer which maintains a preferred dynamic range for a sensor which employs pH changes for detection of analytes. Where a pH change is employed with a pH indicator for detecting the analyte, a buffer is preferably used in the interrogated sample solution to set the dynamic range of the sensor. The buffer allows the dynamic range of the sensor to be targeted to whatever pH changes would be expected from the anticipated concentration range of the analyte in the sample solution. Thus, the buffer makes sure that the pH change which is anticipated falls within the dynamic range of interest. In another embodiment, the sample solution may further comprise ion salts for initially establishing the ionic strength of the sensor sample solution so as to approximate the ionic strength of the ambient fluid medium. By approximately matching the ionic strengths of the two fluids, equilibration of the sensor with the ambient fluid medium is facilitated which provides for faster sensor deployment and more stable initial measurements.

It is well known in the art that most indicator dyes undergo photobleaching and loss of activity upon exposure to a threshold intensity of light. Thus, repetitive light exposures of the dye during continuous monitoring and measurement of analytes will cause depletion of active dye within the sensor and corresponding loss of signal during continuous operation, significantly limited the useful life of the sensor. The sensor of the present invention overcomes this limitation by providing excess indicator dye in a dye reservoir which continuously replenishes the sensor sample solution with active dye during extended sensor operation. The surplus dye in the dye reservoir of the present invention is optically isolated from the optical interrogation zone of the sensor and thereby protects the surplus dye from photobleaching during extended operation. Since the dye solution in the reservoir is in fluid contact with the optical interrogation zone, the reservoir of active dye is able to continuously replenish spent dye in the interrogated sample solution which has been rendered inactive by photobleaching from repetitive exposure to excitation light during continuous analyte monitoring.

An additional unique feature of the present sensor design is that, since the dye reservoir solution and interrogated sample solution are in fluid contact, the two solutions are essentially fully equilibrated at all times with respect to the dissolved analyte, pH, ionic strength and dye. This distinct feature offers the additional advantage of enhanced sensor stability and improved sensor response time since signal drift is minimized by prior equilibration of the two solutions where there is no additional extended sensor stabilization period required for equilibration of analyte, pH, ionic strength or dye concentration in the interrogated sample solution prior to taking a measurement of the analyte concentration.

In one preferred embodiment, the indicator dye is a ratiometric dye which permits measurement of emitted light at two wavelengths where wavelength intensity ratios may be employed for monitoring excitation source or system instabilities for correction of signal spikes or instrument drift during extended operation. In one preferred embodiment, an indicator dye with an isobestic point is employed. An isobestic point is a wavelength at which the absorbance of the dye is pH independent and is directly proportional to dye concentration. With this embodiment, changes in indicator dye absorbance may be employed to monitor photobleaching of the indicator during operation and assess the remaining lifetime of the sensor.

The sensor of the present invention additionally employs an analyte permeable membrane which permits transport of a target analyte from the ambient fluid medium to the interrogated sample solution in the optical interrogation zone of the sensor. While this membrane may be either semi-selective or selective for the target analyte, there is no requirement that the membrane be selective toward the target analyte nor preferentially transport the target analyte. This is due to the choice of sensor indicator dye which is typically selected based on dye selectivity and sensitivity for the target analyte. Preferably, the permeable membrane restricts or impedes transport of the indicator dye from the interrogated sample solution to the ambient fluid medium so as to prevent premature loss of the indicator from the sensor during operation. In alternative embodiments, a semi-selective or selective permeable membrane may be employed which restricts transport of interfering analytes from the ambient fluid medium to the interrogated sample solution which could potentially interfere with detection of the target analyte.

Details and examples of the above features and embodiments are described in the following sections with respect to the various elements which comprise the sensor of the present invention.

Individual Optical Fiber Strand

The fiber optic chemical sensor of the present invention comprises commercially available optical fibers which are conventionally known and available. Alternatively, while individual customized optical fibers may be prepared in accordance with the practices and techniques reported in the scientific and industrial literature, these variations are also deemed to be conventionally known to one of ordinary skill in the art. Typically, optical fibers are made from flexible, transparent glass or plastic compositions which have a high degree of optical clarity and are capable of conveying light long distances with minimal optical loses and low signal-to-noise ratios. Thus, light of a certain wavelength characteristic introduced at one end of the fiber may be faithfully conveyed through the fiber and transported long distances to the opposite end while maintaining the integrity of the initial light.

The sensor of the present invention may employ single optical fiber strands, bundled fibers or preformed, unitary fiber optic arrays or imaging fibers comprising a plurality of coaxial fibers joined along their lengths. Where preformed, unitary fiber array is employed, the arrangement of individual fiber strands may be uniform and coherent, as with an imaging fiber, or incoherent, with random or semi-random arrangement of the individual fibers. In a preferred embodiment, at least one individual optical fiber strand is employed.

A typical optical fiber strand comprises a single, individual optical fiber of uniform cross-section and any desirable length. Cross-sectional diameters of commercially available fibers typically range from 5 µm to 500 µm although sub-micron diameters are also available. While circular cross-sections are most typically employed, other geometric or asymmetrical cross-sectional shapes may be employed. These fibers are routinely employed in lengths ranging from centimeters to meters to kilometers depending on the application. While the end surfaces of such fibers are typically smooth and planar, the surfaces may be concave, convex, irregularly shaped, etched or otherwise optionally treated, for example by a silanization process, for a specific application. Where the terms "proximal" and "distal" are used to identify an end surface of an optical fiber, these terms are interchangeable in describing the fiber unless otherwise employed to clarify the relative positions of fiber ends or to note distinctions between the two ends of an individual fiber.

Typically, the exterior surface of individual optical fibers are clad axially along their length with a cladding material having a lower refractive index than the fiber core. The cladding material prevents optical losses to the ambient environment. The cladding material may thus be comprised of a variety of materials and chemical formulations including various glasses, ceramics, polymers, and metal coatings. The manner in which the optical fiber is clad is inconsequential for the purpose of the present invention as many methods of deposition, coating, plating, and extrusion are conventionally known and commercially available. Where individual optical fibers are exposed to harsh environmental, chemical or mechanical conditions, the fibers may optionally be protected with a protective sheathing material comprised of metal, glass, ceramic, polymeric or composite materials.

It will be recognized and appreciated that the range and diversity of dimensional and configurational options for the optical fiber strand is limited only by the user's ability to subsequently provide an optically interrogatable region at one end of the fiber for optical measurement of a target analyte in a fluid sample.

Indicator Dyes:

A wide variety of indicator dyes for measuring pH and detecting various chemical analytes, including gases, cation species, and anion speciess are conventionally known and commercially available. Two particularly useful references for the identification and selection of indicator dyes for applications in chemical sensors are *Indicators*, E. Bishop (ed.), Pergamon Press (New York 1972) and *Handbook of Fluorescent Probes and Research Chemicals*, Richard P. Haugland, $6^{th}$ ed., 1996, Molecular Probes Inc. (Eugene, Oreg.), both of which texts are expressly incorporated by reference herein.

While indicator dyes used in the sensor of the present invention may be either a chromophore-type or a fluorophore-type, a fluorescent dye is preferred because the strength of the fluorescent signal provides a better signal-to-noise ratio and improved sensitivity and detection limits. Where fiber optic chemical sensors are to be deployed for extended periods of time, the lifetime of the sensor may be compromised and limited due to degradation or destruction of the indicator dye due to either photobleaching or reaction. Most dye indicators undergo an irreversible reaction and loss of signal due to photobleaching of the fluorophore during high intensity illumination or repeated optical cycling. Photobleaching may be avoided my minimizing the exposure of the dye to high intensity illumination or optical cycling or maximizing detection sensitivity so that a lower excitation light intensity may be employed. Alternatively, commercially available antifade agents, such as SlowFade™ or ProLong™ (Molecular Probes, Eugene, Oreg.) may be employed. In the present invention, two approaches to minimization of photobleaching are employed to extend the lifetime of the dye indicator and sensor. The sensor design provides for a reservoir of excess dye indicator which can continuously replenish spent dye during the operational lifetime of the sensor. The dye in the reservoir is optically isolated from the light interrogation region of the sensor to avoid exposure of the surplus dye in the reservoir to unnecessary illimunation and optical cycling from exposure to excitation light illumination. Alternatively, a ratiometric dye indicator may be used for monitoring and elimination of signal drift or distortion caused by light source or system instrumentation instabilities. Where the indicator dye has an isobestic point, photobleaching of the dye may be monitored over the lifetime of the sensor by measuring the absorbance of the dye at the isobestic wavelength.

In a preferred embodiment, ratiometric indicator dyes are employed for extending sensor lifetime. Ratiometric indicator dyes are typically free and ion-bound forms of fluorescent ion indicators that have either two different emission or two different excitation peaks. The advantage of these dyes is that the intensity ratio of two peak signals may be used to monitor association equilibrium and calculate ion concentrations. Ratioing of peak signals eliminates distortions in measurement data caused by photobleaching and illumination instability. Specific examples of ratiometric dye indicators which are particularly useful include, but are not limited to SNARF®, SNAFL®, BCECF, Fura-2 and Indo-1, all of which are available from Molecular Probes (Eugene, Oreg.). Additional dyes which are conventionally known in the art and may be employed as indicator dyes in the present invention are those found in U.S. Pat. No. 5,512,490 to Walt, et al., of which Table 3, Table 4, Table 5, Table 6 and Table 11 are incorporated herein by reference. Examples of indicator dyes which have utility for specific analytes in sensing applications are provided in Table 1

In one embodiment, the indicator dye may be conjugated with high molecular weight polymer. Conjugated dyes have utility where the unconjugated indicator is able to transport across the analyte permeable membrane, leaving the sensor and being lost to the sample medium. By increasing the molecular weight and size of the indicator by conjugation with a polymer, the indicator's mobility is restricted and it is confined within the sensor by the analyte permeable membrane and is unable to transport through the membrane. Indicators which are conjugated with dextran are commercially available in a wide range of molecular weights from Molecular Probes (Eugene, Oreg.). Membrane transport and loss of dye may also be prevented by employing charged indicators or indicators conjugated with charged polymers.

TABLE 1

| TARGET ANALYTE | INDICATOR DYE | NOTES ($\lambda_{ab}/\lambda_{em}$) |
|---|---|---|
| pH Sensors based on: | seminaphthofluoresceins | e.g., carboxy-SNAFL |
| | seminaphthorhodafluors | e.g., carboxy-SNARF |
| | 8-hydroxypyrene-1,3,6-trisulfonic acid | |
| | fluorescein | |
| $CO_2$ Sensors based On: | seminaphthofluoresceins | e.g., carboxy-SNAFL |
| | seminaphthorhodafluors | e.g., carbody-SNARF |
| | 8-hydroxypyrene-1,3,6-trisulfonic acid | |
| Metal Ions Sensors based on: | desferriozamine B | e.g., Fe |
| | cyclen derivatives | e.g., Cu, Zn |
| | derivatized peptides | e.g., FITC—Gly—Gly—His, and FITC—Gly His, Cu, Zn |
| | fluorexon (calcine) | e.g., Ca, Mg, Cu, Pb, Ba |
| | calcine blue | e.g., Ca, Mg, Cu |
| | methyl calcine blue | e.g., Ca, Mg, Cu |
| | ortho-dianisidine tetracetic acid (ODTA) | e.g., Zn |
| | bis-salicylidene ethylenediamine (SED) | e.g., Al |
| | N-(6-methoxy-8-quinolyl-p-toluenesulfonamine (TSQ) | e.g., Zn |
| | Indo-1 | e.g., Mn, Ni |
| | Fura-2 | e.g., Mn, Ni |
| | Magnesium Green | e.g., Mg, Cd, Tb |
| $O_2$ | Siphenylisobenzofuran | 409/476 |
| | Methoxyvinyl pyrene | 352/401 |
| Nitrite | diaminonaphthaline | 340/377 |
| NO | luminol | 355/411 |
| | dihydrorhodamine | 289/none |
| $Ca^{2+}$ | Bis-fura | 340/380 |
| | Calcium Green | visible light/530 |
| | Fura-2 | 340/380 |
| | Indo-1 | 405/485 |
| | Fluo-3 | visible light/525 |
| | Rhod-2 | visible light/570 |
| $Mg^{2+}$ | Mag-Fura-2 | 340/380 |
| | Mag-Fura-5 | 340/380 |
| | Mag-Indo-1 | 405/485 |
| | Magnesium Green | 475/530 |
| | Magnesium Orange | visible light/545 |
| $Zn^{2+}$ | Newport Green | 506/535 |
| TSQ | Methoxy-Quinobyl | 334/385 |
| $Cu^+$ | Phen Green | 492/517 |
| $Na^+$ | SBFI | 339/565 |
| | SBFO | 354/575 |
| | Sodium Green | 506/535 |
| $K^+$ | PBFI | 336/557 |
| $Cl^-$ | SPQ | 344/443 |
| | MQAE | 350/460 |

In a preferred embodiment, the fluorescent pH indicator, 5' (and 6')-carboxyseminaphthofluorescein (c-SNAFL-1), was utilised as an indicator dye. Since this indicator has dual emission wavelengths, it may be used for ratiometric measurements at both wavelengths to monitor system instabilities and photobleaching effects.

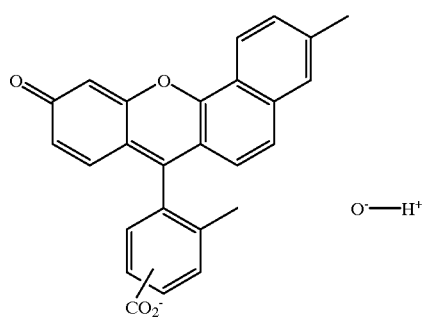

The properties of the indicator are described elsewhere [D. R, Gabor, G., Goyet, C. *Anal. Chim. Actca* 1993, 274, 47; Szmacinski, H., Lakowicz, J. R. *Anal. Chem.* 1993, 65, 1668; Mordon, S., Devoisselle, J. M., Soulie, S. *J. Photochem. Photobiol. B. Biol.* 1995, 28 (1), 19] and are summarized in Table 2.

An important feature of the dye is that it possesses two emission peaks when excited at 488 nm. These peaks are centered at 540 nm and 620 nm and result from the protonated and deprotonated forms of the dyes respectively. This dual wavelength feature of the dye makes it particularly suitable for use in a ratiometric mode which accounts for system instabilities, such as photobleaching and lamp intensity fluctuations. This dye also has an isosbestic point at 625 run (Ex.=488 nm) which can be used for ratiometric measurements to assess the extent of dye photobleaching over time.

FIG. 1 shows the emission spectra of c-SNAFL-1 in distilled water (25° C.) at various pH values using 488 nm excitation light. The pH values shown in FIG. 1 are taken from the titration curve data for water shown in FIG. 2. The maxima centered at 540 nm and 620 nm arise from the protonated and deprotonated forms of the dye respectively.

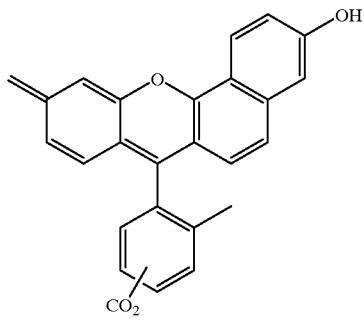

$$pH = pK_{in} - \log\left(\frac{I}{I_o - I}\right) \quad [5]$$

or, in terms of I:

$$I = \frac{I_o}{1 + (10^{pK_{in} - pH})^{-1}} + B \quad [6]$$

In this equation the additional term B is the background fluorescence of the system and is an experimentally-derived value. I can also be the ratio of the fluorescence intensities of the protonated and isosbestic forms, where. $I = I_{545}/I_{isos}$

TABLE 2

Physical and chemical properties of carboxy-SNAFL-1 (at 21° C.)

| property | refs. 12, 13 and 14 | in H₂O | in 0.67M NaCl | sensor (at 12° C.) (calculated) |
|---|---|---|---|---|
| Absorbance | 481 nm (acid) | — | — | — |
|  | 510 nm (acid) | — | — | — |
|  | 539 nm (base) | — | — | — |
| Emission | 542 nm (acid) | 545 | 542 | 545 |
| (Ex. = 488 nm) | 615 nm (isos) | 632 | 624 | — |
|  | 623 nm (base) | 618 | 620 | 610 |
| $pK_{in}$ | 7.75 | 8.01 | 7.67 | 7.98 |
| $I_{(543/623)}$ (max) | 6.13 | 5.41 | 5.27 | 5.54 |
| $I_{(543/623)}$ (min) | 0.09 | 0.145 | 0.129 | — |
| $\Delta pH/\Delta T/°\ C.^{-1}$ | 0.0192 | — | — | — |
| $\Delta H°/kcal\ mol^{-1}$ | 3.78 | — | — | — |
| $\Delta S°/cal\ mol^{-1}\ K^{-1}$ | −22.6 | — | — | — |
| $pK_1$ | — | — | — | 6.53 |
| $[HCO_3^{3-}]/\mu M$ | — | — | — | 158 |

The fluorescence intensity of c-SNAFL-I results from the following equilibria established in aqueous solution:

$$HIn \xrightleftharpoons{K_{in}} H^+ + In^- \quad [12]$$

where HIn and In⁻ are the protonated and deprotonated forms of the of the dye respectively, and $K_{in}$ is the acid dissociation constant for the dye in its ground electronic state:

$$K_{in} = \frac{h\,d}{dh} \quad [2]$$

where d=[In⁻] and dh=[HIn] and $$dh_T = d + dh \quad [3]$$

where $dh_T$ is the total indicator concentration.

Equation 3 can be rewritten in the form of the well known Henderson-Hasselbach equation:

$$pH = pK_{in} - \log\left(\frac{dh}{d}\right) \quad [4]$$

Where the fluorescence intensity I=dh and $I_0 = dh_T$, the fluorescence intensity when the indicator is fully undissociated, Equation 4 becomes:

Indicator Dye Solution

Figure 3:
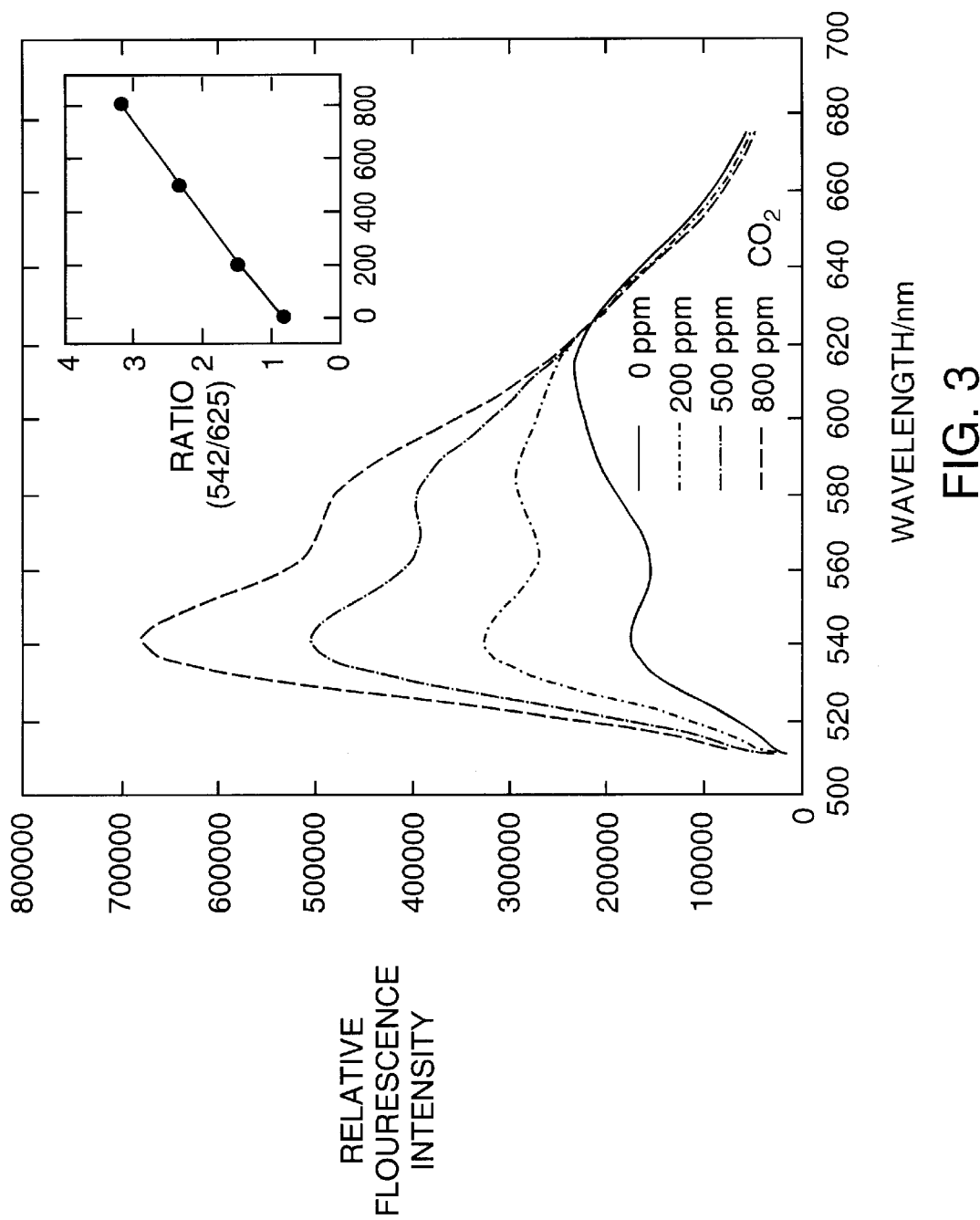
FIG. 3 shows an emission spectra of the $pCO_2$ indicator solution at various $pCO_2$ tensions when subjected to excitation at 488 nm. The inset shows the corresponding calibration curve using the ratio of the emission intensities at 542 nm and 625 nm.

In one embodiment, an indicator solution for the sensor was prepared for a CO₂ sensor by making a 100 μM c-SNAFL-1 (Molecular Probes Inc., Eugene, Oreg.) solution in 0.67 M NaCl containing approximately 150 μM bicarbonate ions. The solution was bubbled with 10% CO₂ in N₂ for 10 minutes. to generate carbonic acid. The final pH of the solution was adjusted to 8.2 using I M NaOH. The solution was stored at 4° C. in the dark. FIG. 3 shows an emission spectra of the pCO₂ indicator solution at various pCO₂ tensions when subjected to excitation at 488 nm. CO₂ containing gas compositions were bubbled through the indicator solution which was held at room temperature. The inset shows the corresponding calibration curve using the ratio of the emission intensities at 542 nm and 625 nm.

Indicator Support Membrane

A key feature of the sensor of the present invention is to extend sensor lifetime by providing excess indicator dye which continuously replenishes spent, photobleached dye. In one sensor embodiment, excess dye indicator solution is confined in an excess dye reservoir comprised of an indicator support membrane. Alternatively, the dye indicator is confined in a chamber formed by the sensor housing and an indicator membrane provides for both containment of excess dye in the chamber as well as transport of dye from the chamber, through the membrane, to the optical interrogation zone to replenish spent dye consumed by aging photobleaching or reaction.

The primary requirement of the indicator membrane material is that it allow transport of dye solution between the dye reservoir and interrogation zone, that it be non-reactive toward the dye, analyte and interrogated sample fluid, and that it not generate any acid or base. Any suitable material, glass, metal, ceramic, polymer or composite, may be employed as an indicator membrane providing the material meets the above requirements. The indicator membrane may be provided as a thin or thick film material, as a sheet material, woven or laminated fiber or cloth material. In a prefered embodiment, a permeable polymer material is employed as the indicator membrane. Particularly useful polymeric materials for use as an indicator membrane include, but are not necessarily limited to poly-N-vinyl pyrrolidone, GoreTex®, cellulose acetate, dialysis membranes with different molecular weight cutoffs, cellulose nitrate, PTFE, Teflon, polysulfones, polycarbonates, polyurethanes, polyhdroxyethylmethacrylates, nylons, polyethylene glycols, and derivatives of the above.

In a preferred embodiment, the fluorescent pH indicator, 5' (and 6')-carboxyseminaphthofluorescein (c-SNAFL-1) solution was immobilized and supported by a polymer film comprising poly-N-vinyl pyrrolidone (NVP). The polymer was prepared by the photopolymerization of N-vinyl-2-pyrrolidone monomer stock solution. The stock solution contained 0.5 ml N-vinyl-2-pyrrolidone monomer, 10 $\mu$l ethylene dimethacrylate crosslinker, 0.5 ml pH 7.3 phosphate buffer, and 30 mg benzoin ethyl ether photo initiator. This solution was degassed with argon and 100 $\mu$l was placed on a microscope slide and covered with a coverslip. The slide was exposed to long wavelength UV light for 5 minutes. The slide was then immersed in distilled water. The fragile polymer film was removed carefully from the glass and placed in the indicator solution and left 24 hours before use.

Analyte Permeable Membrane

One surface of the sensor assembly is preferably covered by permeable membrane which is permeable to a target analyte of interest and preferably impermeable to the indicator dye. The primary requirements of this membrane are that it allows transport of the target analyte from the ambient fluid medium to the interrogated sample solution in the optical interrogation zone of the sensor and that it restricts transport and loss of indicator dye from the sensor to the ambient fluid medium. The membrane is prefereably insoluble in either fluid. In one embodiment, the permeable membrane may be semi-selective or selective for the target analyte and impedes transport of interfering analytes from the ambient fluid medium to the sensor sample fluid. While any glass, ceramic, porous metal, composite or polymer membranes may be employed which satisfy these requirements, in a preferred embodiment, a permeable polymeric membrane is employed. Particularly useful polymeric materials for the permeable membrane include, but are not limited to, cellulose acetate, dialysis membranes having different molecular weight cutoffs, cellulose nitrate, polyethylenes, PTFE, teflon, polyvinyl chloride, silicone polymers, poly vinylidene chlorides, poly sulfones, polycarbonates, polyurethanes, poly hydroxyethylmethacrylate, nylons, polyethylene glycols and derivatives of the above.

Sensor Design and Fabrication

FIG. 4 is a schematic of the over all sensor design. FIG. 4a shows the overall sensor housing design and associated optical fiber. FIG. 4b shows details of the optical interrogation region, dye support member and dye reservoir. FIGS. 4c and 4d are schematic cross-sectional view of alternative dye reservoir and sensor configurations.

The sensor shown in FIG. 4 comprises a sheathed optical fiber 200 inserted in a bore hole in in a housing member 205. The exposed length of the fiber 200 is protected by a conventional fiber sheathing material comprised of fiber-reinforced plastic. The sheathing on the distal end 202 of the fiber 200 is removed and the fiber is inserted into the housing and secured with epoxy cement such that the distal end surface 202 of the fiber 200 is flush with the end surface of a fiber sleeve 215 machined in the housing 205. A dye reservoir 220 is formed by machining an annular cavity in the housing around the fiber sleeve 215. The cavity forming the dye reservoir 220 is filed with excess indicator solution and a permeable indicator dye support membrane 225 is positioned over the cavity forming the dye reservoir 220. The indicator support membrane 225 may be either disk-shaped and positioned across the reservoir 220, fiber sleeve 215 and distal end 202 of the fiber 200 (as shown in FIG. 4b), or, alternatively, the indicator support membrane 225 may be annulus-shaped and positioned at the end of the annular cavity which forms the dye reservoir 220 (as shown in FIG. 4c). In an alternative sensor configuration shown in FIG. 4d, the indicator support membrane 225 may be shaped as an elongated annular cylinder, extending throughout the entire reservoir cavity 220. An analyte permeable membrane 230 is then placed over the sensor assembly and held in place by a membrane holder 235. The membrane holder may be either clamped to or threaded on the housing to hold the permeable membrane in place. Prior to placement of the permeable membrane 230, the reservoir cavity 220 is filed with excess indicator dye solution. In the immediate vicinity of the distal end 202 of the fiber 200, an optical interrogation zone 240 is formed by the region or volume element illuminated by excitation light which is transmitted through the fiber 200 emerges from the distal end 202 of the fiber 200 during an optical measurement. The diametric dimension of the optical interrogation zone 240 is approximately defined by the numerical aperture of the fiber with some slight variation due to divergence of the excitation light when emerging from the end of the fiber.

In one sensor embodiment used for low-level dissolved $CO_2$ sensing, a 400 $\mu$m diameter single core fiber was employed as the optical fiber 200. The fiber 200 was inserted into a PEEK™ (Oxford Electrodes, Abington, UK) housing 205, a chemically stable, mechanically robust and machineable polymer of poly etheresterketone. Other housing materials may be employed which meet these material requirements. The fiber was secured in the housing with epoxy cement. A 100 um thick disk of N-vinylpyrrolidone (NVP) polymer, presoaked in indicator solution, was employed as an indicator support membrane 225 and was positioned between the fiber end surface 202 and an outer gas permeable membrane 230 made from 10 $\mu$m thick PTFE (Goodfellows Corp., Berwyn, Pa.). The indicator support membrane 225 was prepared by cutting a 3 mm diameter NVP disk using a small cork borer. The indicator support 225 was adapted to fit a recess which formed a dye reservoir 220 in the sensor housing 205 and was held in place by the membrane 230 and membrane holder 235.

The porous NVP polymer provided a conduit for the natural convection of the indicator solution. A local cavity which was formed between the fiber end 202 and the support 225 was estimated to contain approximately 50 $\mu$l volume of indicator solution which served as an interrogated sample solution. This cavity provided a fixed optical path length for the optical interrogation zone 240.

The NVP indicator support membrane 225 material was found to be particularly useful for salt water measurements of dissolved $CO_2$. After screening numerous hydrogel candidates, this polymer was chosen because of its hydrolytic stability in seawater. Acrylate-based polymer systems were found to hydrolyze slowly causing the equilibrium pH of the indicator solution to change making the sensor insensitive to $CO_2$.

Figure 4A:
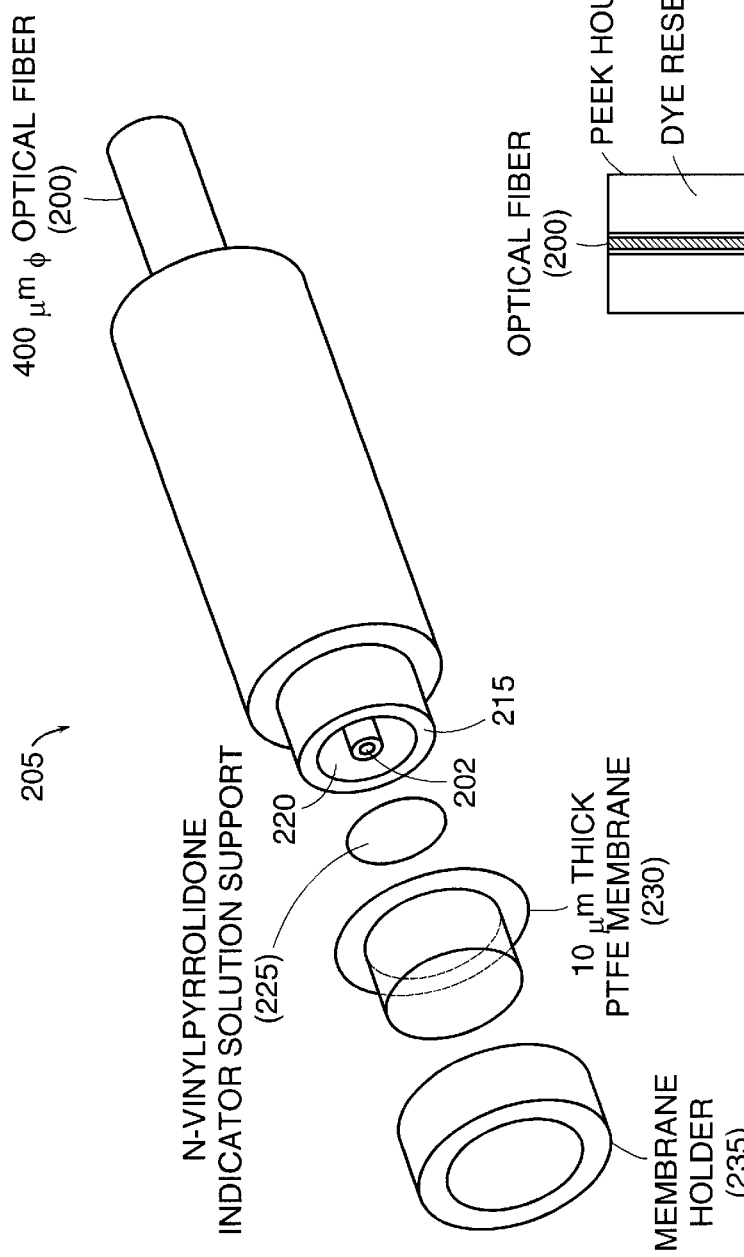
FIGS. 4a–c show a schematic of the sensor construction.
Figure 4B:
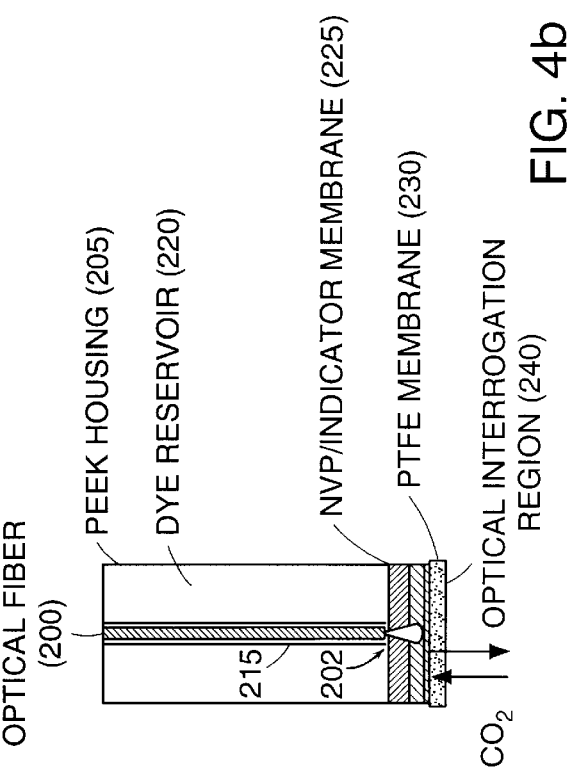
Figure 4C:
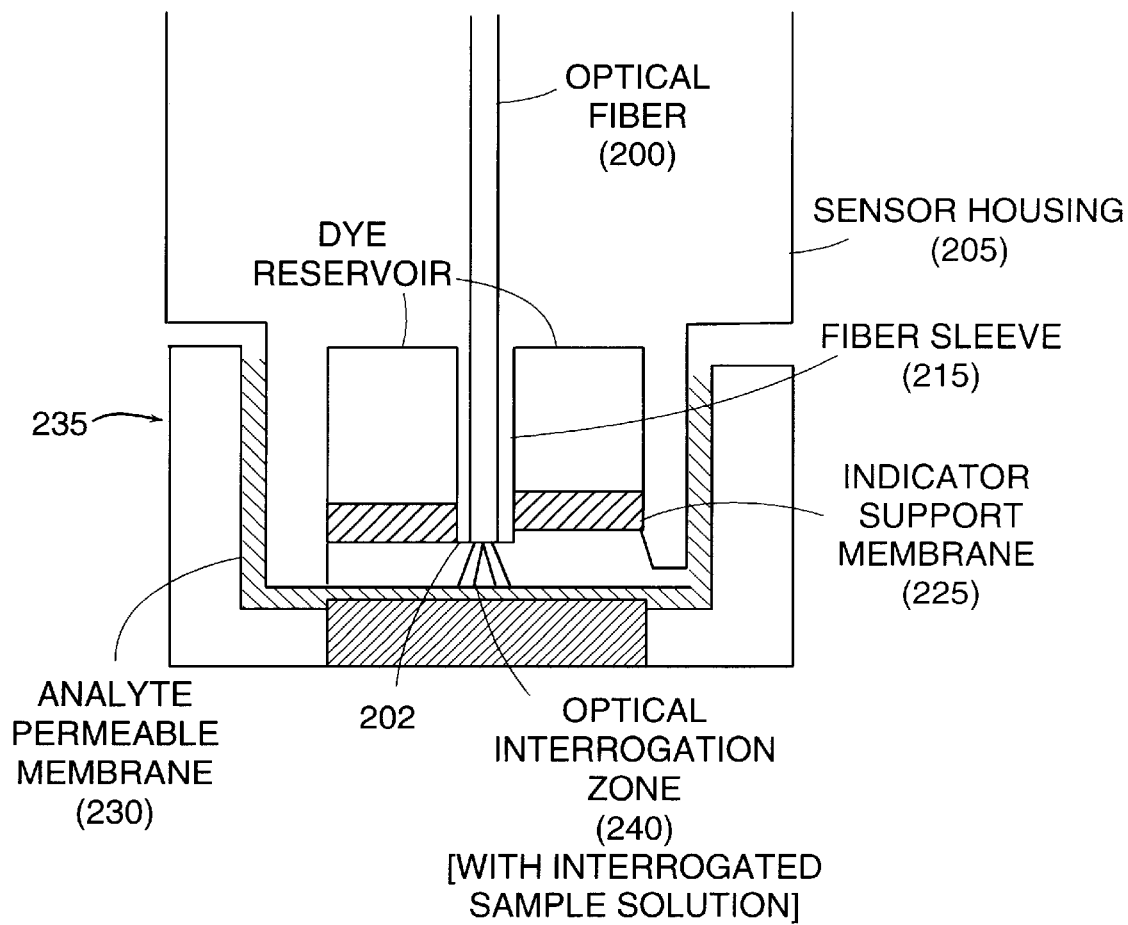
Figure 4D:
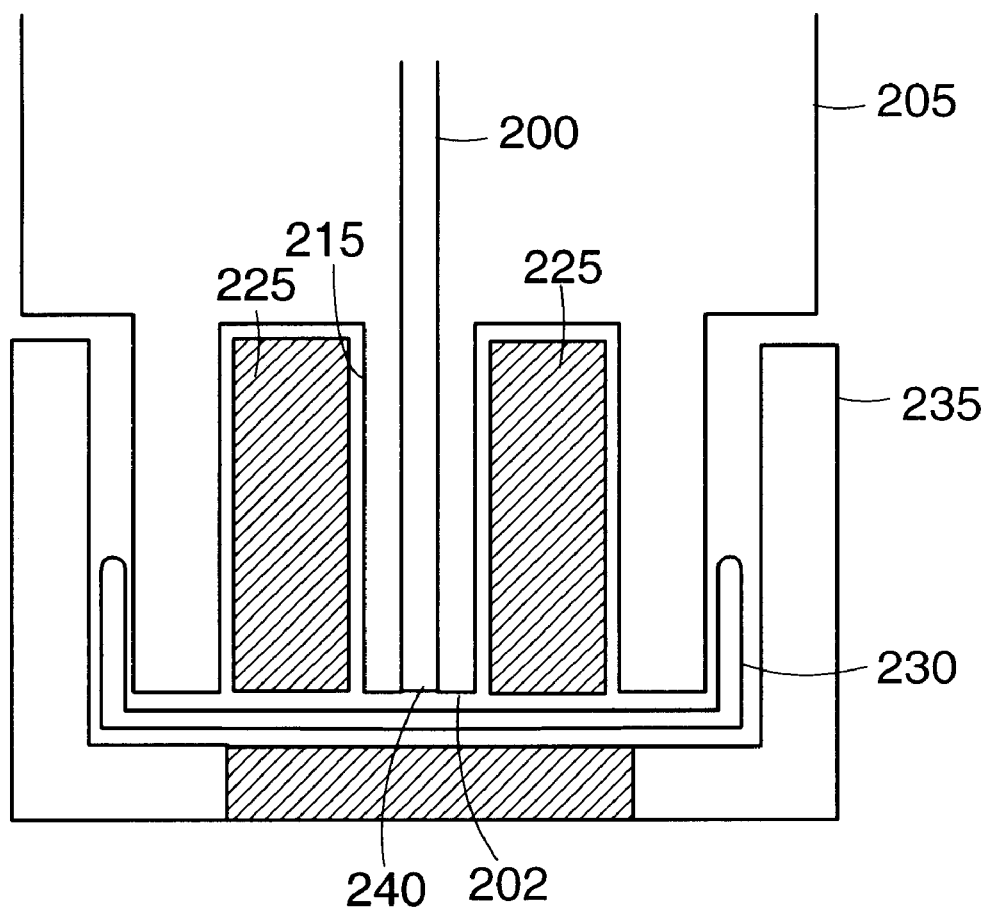

As shown in FIG. 4b, the excitation light which emerges from the fiber end 202 interrogates a relatively small optical interrogation zone 240 in a central region of the NVP indicator support membrane 225. The analyte diffuses through the entire membrane and equilibrates with the indicator dye solution in the dye reservoir 220. The response time of the sensor is typically related to how long it takes for the analyte to equilibrate with the interrogated sample solution in the optical interrogation zone 240 in front of the distal end 202 of the fiber 202. The additional permeable indicator support membrane 225 volume outside of the interrogation zone 240, assists in this equilibration by providing a pathway for lateral diffusion of analyte and dye between the interrogated sample solution in the interrogation zone 240 and excess dye solution within the dye reservoir 220. Excess dye from the dye reservoir 220 is continually replenishing spent indicator in the optical interrogation zone 240 so that photobleaching of the dye in front of the fiber does not compromise the sensor signal. The dye reservoir 220 in one embodiment contained approximately 4000 times as much dye as was contained in the interrogated sample solution in the optical interrogation zone 240. It is anticipated that any particular volume of the dye reservoir 220 may be selected in order to provide as much excess indicator dye as is required for the anticipated sensor lifetime.

After the sensor is first prepared, it is preferably stored in a solution which closely matches the ionic strength of the ambient fluid medium in which the sensor will be deployed so as to provide for rapid equilibration of the sensor with the ambient fluid medium prior to taking measurements. During this pre-equilibration period, the osmotic pressure on both sides of the analyte permeable membrane may be balanced.

Sensor Characterization and Measurements

The properties and performance characteristics of sensors were extensively evaluated in both preliminary laboratory screening and calibration tests and subsequent deployment in oceanographic field tests. The instrumentation and testing for each phase of development is provided below.

Laboratory Evaluations

Instrumentation

Figures 5A, 5B:
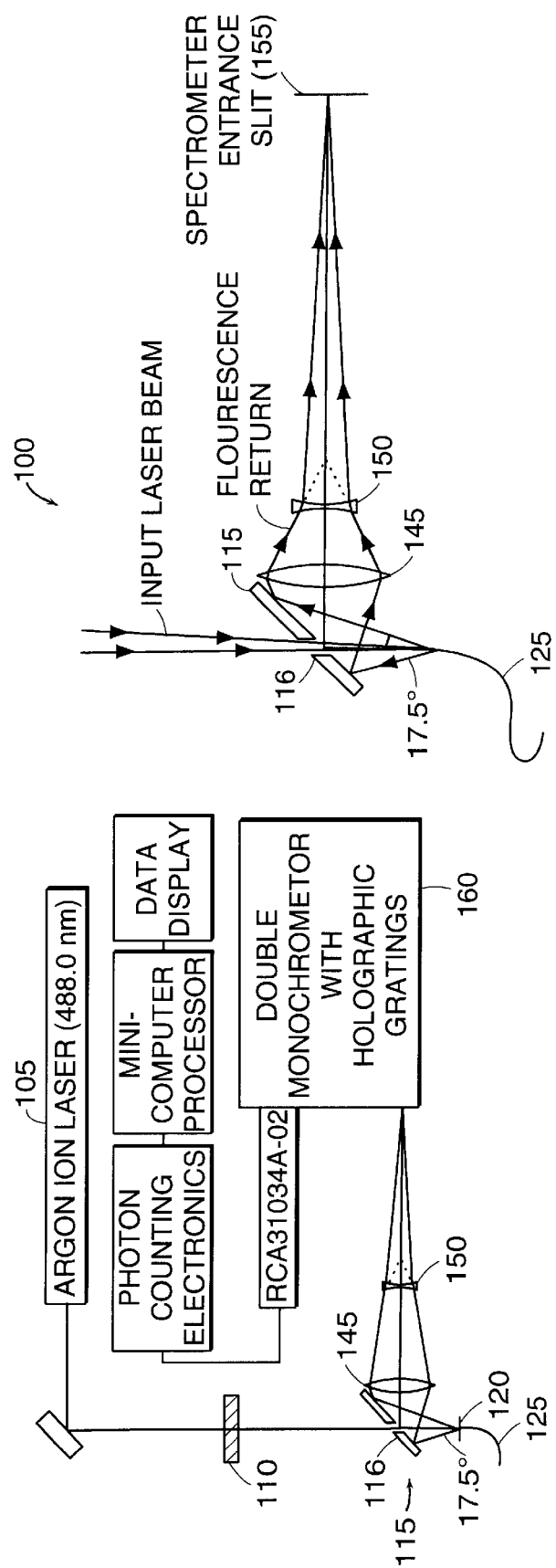
FIG. 5 is a schematic block diagram of the laboratory measurement system and apparatus.

Prior deployment in field tests, sensors were subjected to extensive laboratory testing and evaluation to determined their response properties and performance characteristics under varying environmental conditions, such as temperature and pH variation. Sensor excitation and emission spectra were performed with the apparatus and instrumentation shown schematically in FIG. 5. This fiber-optic double monochromater fluorescence measurement system has been described in detail previously [Munkholm, C. and Walt, D. R., *Talanta*, 1988, 35, 109; Munkholm, C. and Walt, D. R., *Anal. Chem.* 1986, 58, 1427–1430; Hirschfeld, T., Deaton, T., Milanovich, F., and Klainer, S., *Opt. Eng.*, 1983, 22, 527–531].

The measurement system 100 comprises a Spectra Physics Model 162A-04 argon-ion laser 105 which provides excitation light radiation, typically at 488 nm. The excitation light is passed through a neutral density filter 110 and an angled dichroic mirror 115 to the proximal end 120 of an optical fiber 125 which conveys the excitation light to the distal end 130 of the fiber 125 and illuminates an optical interrogation zone 135 comprising a fluid sample volume with an indicator dye and analyte. In the presence of the analyte, the excitation light causes the indicator dye to emit emitted light energy in the optical interrogation zone 135, which emitted light is conveyed by the fiber 125 to the proximal end 120 and is deflected through 90° by the front surface 116 of the angled dichroic mirror 115. The emitted light is then focussed with lenses 145, filtered through a long wavelength, band-pass filter 150, and passed through a slit 155 into a monochromater 160. The resulting wavelength-dispersed signal is measured with a Pacific Instruments Model 126. photo-counting detection system. The intensity of the excitation light is measured in photon counts per second as either a function of time or of wavelength examined.

Sensor Calibration

The calibration and operation of the sensor operation of the sensor is based on the Severinghaus electrode principle. When carbon dioxide crosses the membrane, the pH of the indicator solution is given by the Henderson-Hasselbach equation:

$$pH = pK_{in} - \log\left(\frac{a_T}{b}\right) \quad [7]$$

where $a_T = K_H K_M \, pCO_2$ $K_H$/mol dm$^3$ atm$^{-1}$ is Henry's constant and $K_M$ is the membrane constant. Substituting Equation 7 into Equation 5 and rearranging gives:

$$I = \frac{I_o}{1 + \left(10^{pK_{in} - pK_I + \log\left(\frac{a_T}{b}\right)}\right)^{-1}} \quad [8]$$

for a>0, and $$I = \frac{I_o}{1 + (10^{pK_{in} - pH_O})^{-1}} \quad [9]$$

for a=0, where $pH_o$ is the pH of the indicator solution at zero $CO_2$.

Figure 2:
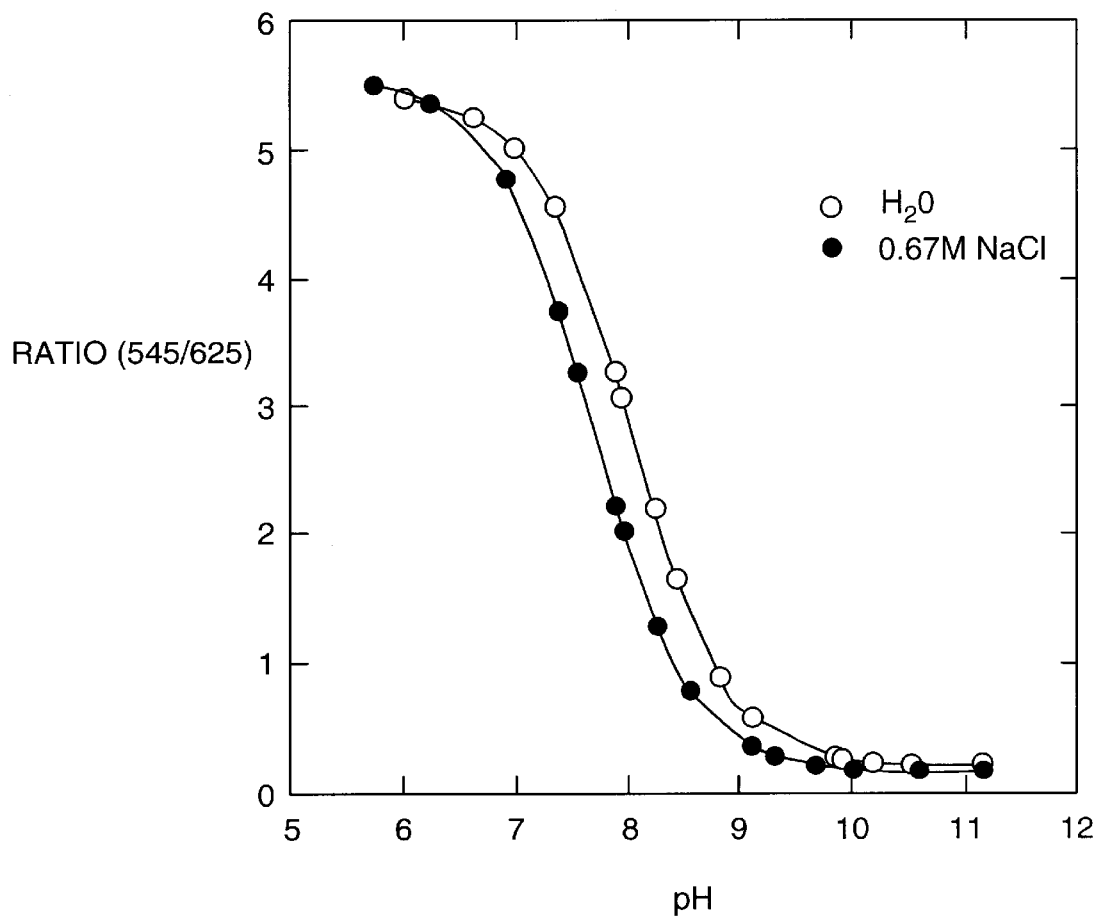
FIG. 2 shows emitted light intensity ratios vs. pH titration curves for carboxy-SNAFL-1 in distilled water and in 0.67 M NaCl. The solid lines are the theoretical curve fits using Equation 6.

FIG. 2 shows a calibration curve for carboxy-SNAFL-1 as emission peak intensity ratio vs. pH. The titration curves are shown for carboxy-SNAFL-1 in distilled water and in a 0.67 M solution of NaCl. The solid lines are the theoretical curve fits using Equation 6. The $pK_a$ for the indicator increases with increasing ionic strength. Experiments were carried out in 0.67 M NaCl because it is necessary to balance the osmotic pressure of the indicator solution in the sensor to that of the test solution. The osmotic pressure of the seawater is equivalent to 0.67 M NaCl.

The solid lines in FIG. 2 are theoretical fits of Equation 5. The results for $I_o$, $pK_{in}$, and B are summarized in Table 2 together with typical values reported elsewhere [Walt, D. R, Gabor, G., Goyet, C. *Anal. Chim. Actca* 1993, 274, 47; DeGrandpre, M. D., *Anal. Chem.* 1993, 65 (4), 331; Whitaker, J. E., Haugland, R. P., Prendergast, R P. *Anal. Biochem.* 1991, 194, 330]. Table 2 shows that increasing the ionic strength decreases $pK_{in}$ [Albery, W. J. and Uttamlal, M. J., *J. Appl. Electrochem.*, 1994, 24, 8] and the maximum fluorescence intensity also decreases with increasing ionic strength.

Figure 6:
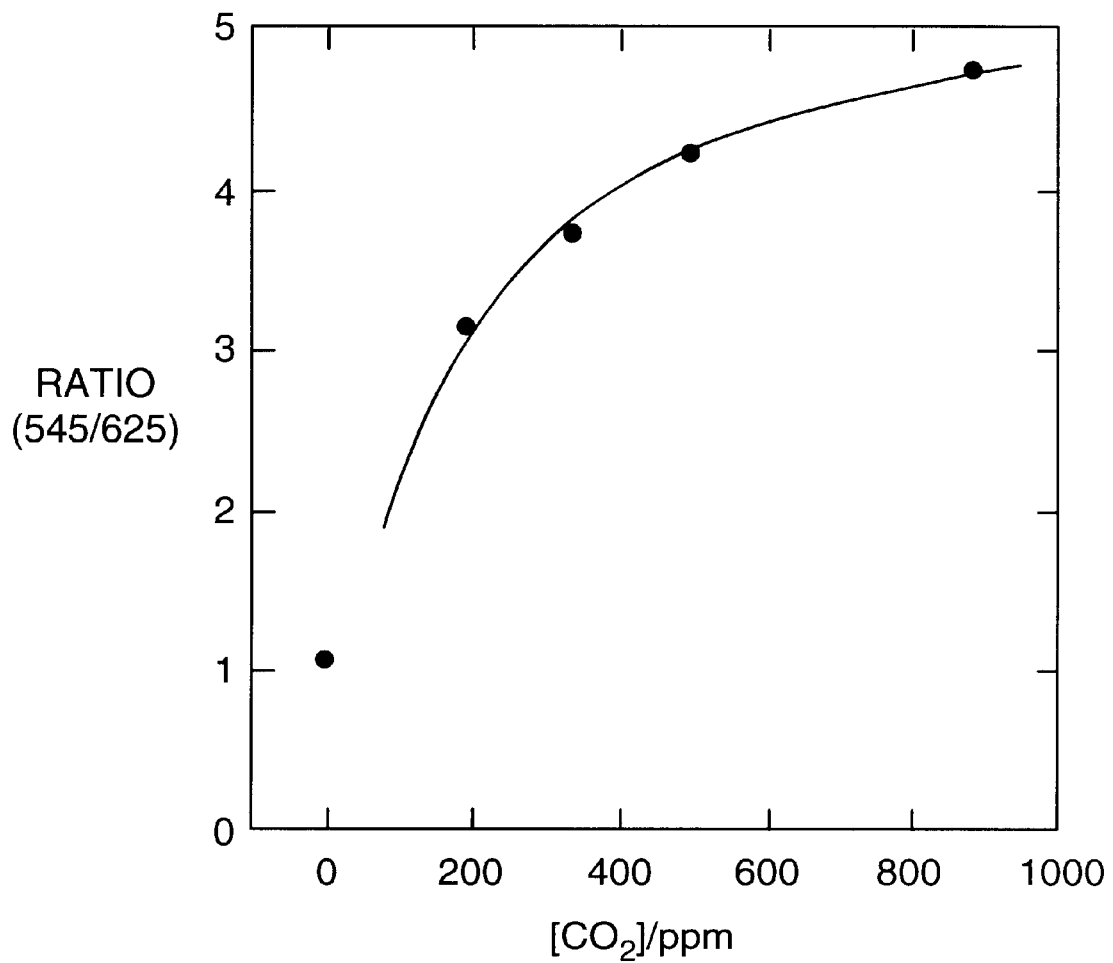
FIG. 6 shows a plot of the sensor calibration for $CO_2$.

FIG. 6 shows the sensor calibration for $CO_2$. The dissolved $CO_2$ concentration was determined using Henry's constant [Cox, J. D., Head A. J. *J Chem. Soc. Faraday Trans.*, 1962, 58, 1839]. The interrogation volume was calculated using a cylindrical volume and does not include the dispersion angle of light exiting the fiber. Also, for this calculation the membrane volume was not corrected for the porosity, or water content, of the membrane. These parameters would have opposite effects. In the calibration, $a_T$ was assumed to equal the dissolved $CO_2$ in the bulk solution, such that $K_M=1$. The sensitivity of the sensor is approximately ±1 ppm.

The theoretical equation relating the fluorescence intensity. ratio to $pCO_2$ was compared to test date and is shown by the solid curve in FIG. 6. From this analysis, the values for the constants in equation 6 were determined and are provided in Table 2. The $pH_o$ value was calculated from Equation 5 using $pK_{in}$ while $I_o$ was derived from the above analysis. There was good agreement between experimental and theoretically-derived data.

Sensor Response Time Characteristics:

The development of performance criteria for new chemical sensors is by necessity application specific. For example, a process control application (fermentor or bioreactor) might require faster response times than the present oceanographic application. Oceanographic $pCO_2$ data will be used to better understand the global $CO_2$ budget and therefore the sensor must be able to monitor slowly changing conditions with good resolution and accuracy. Response times of minutes to hours is acceptable for this application. The response time characteristics for the Severinghaus $pCO_2$ electrode have been described by several workers [Severinghaus, J. W., Bradley, A. F., *J2 Appi. Physiol.* 1956, 13, 515; Hafeman, D. G., Crawford K. L., Bousse, L. J. *J. Phys. Chem.* (1993), 97, 3058; Van der Schcot, B., Bergveld, P., *Anal. Chim. Acta.* (1984), 166, 93; Ross, J. W., Riseman, J. H., Krueger, J A., *Pure. Appl Chem.* (1973), 36, 473]. Much of these previous studies dealt with response time characteristics where concentration step changes were relatively large. In a previous paper, we described the response time characteristics of a $pCO_2$ sensor and showed that they are similar to those of the Severinghaus electrode. The theory predicts that small step changes at low level $pCO_2$ exhibit much longer response times than large step changes because, at low levels, a large proportion of the $CO_2$ crossing the membrane is consumed by the reaction with $H_2O$, $CO_3^{2-}$, $HCO_3$ and the pH indicator dye before equilibrium across the membrane is established. For large step changes only a small fraction of the permeating $CO_2$ is used in this process resulting in a much shorter response time.

Figure 8:
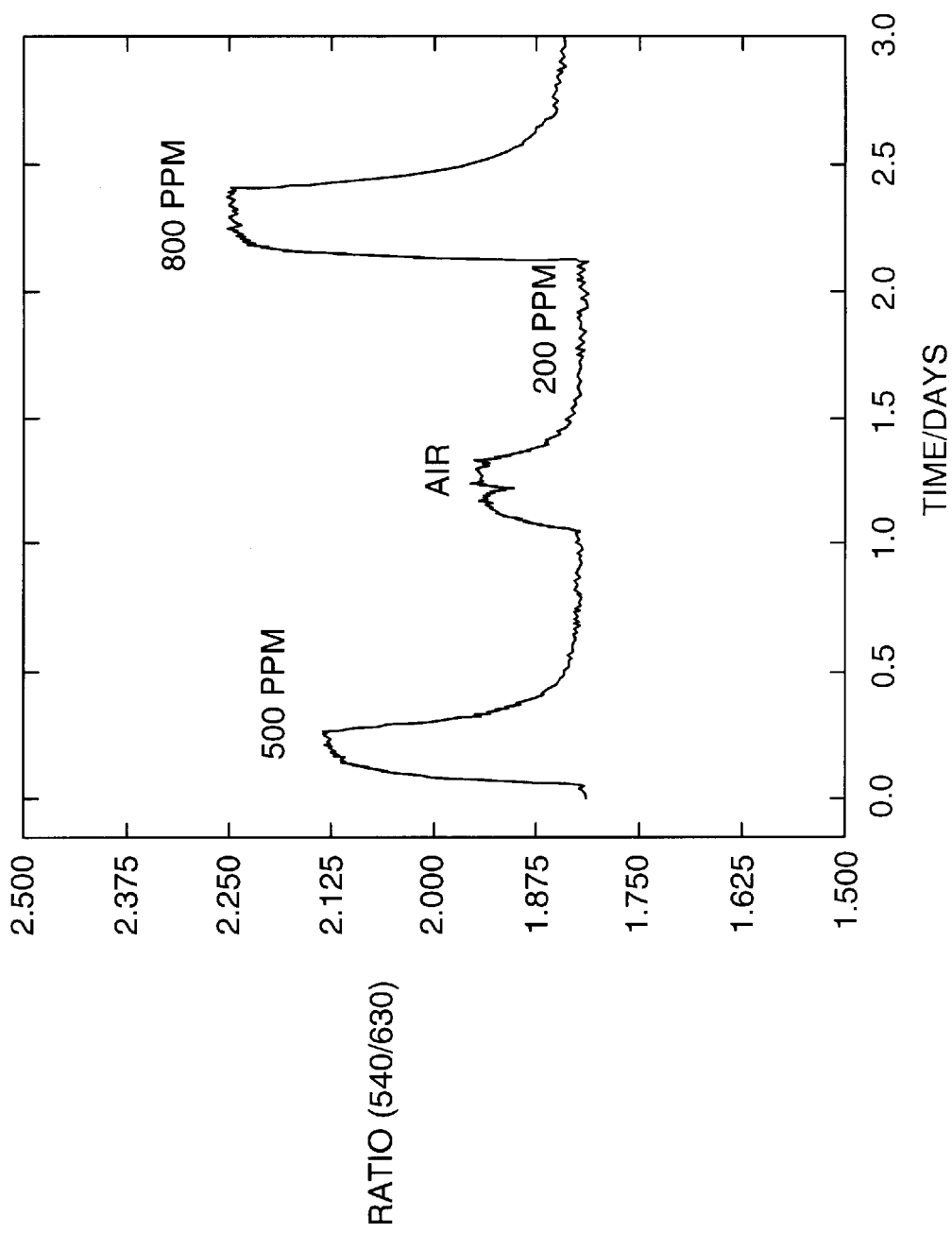
FIG. 8 shows the response time characteristics of the sensor for step changes in $pCO_2$.

FIG. 8 shows the response time profiles for step changes in $pCO_2$ in 0.67 M NaCl at 12° C. Measurements were performed in 0.67 M NaCl at 12° C. The data show that the sensor is very stability over the extended measurement period. These results are summarized in Table 3 and are consistent with the theory described above with small step changes having longer response times than large step changes. The response times are also very much longer than those of high level $pCO_2$ sensors; again, consistent with theory. It is important to note, however, that the sensor responds immediately to even a small change in $CO_2$. The response time of the sensor can be improved by adding carbonic anhydrase to the indicator solution [Donaldson, T. L., Palmer, I-U., *AIChEJ*. (1979), 25 (1), 143]. This enzyme catalyses the $CO_2$ hydration reaction which is the rate limiting step in the sensor response. For the ocean seawater experiments, carbonic anhydrase was not used due to its propensity to denature in during long deployments.

TABLE 3

Response time characteristics (12° C.). The starting $[CO_2]$ for each step change was 200 ppm.

| $\Delta CO_2$ ($[CO_2]_0$ = 200 ppm) | $t_{90}$/min |
|---|---|
| 150 | 130 |
| 300 | 100 |
| 600 | 60 |

Temperature Effects on Sensor Response

In both environmental and process monitoring applications of fiber optic chemical sensors, the ambient temperature is rarely fixed and is frequently subjected to periodic fluctuations. For example, in oceanographic monitoring, the temperature of ocean water is subject to daily temperature fluctuations caused by daytime solar heating, radiational cooling at night, ocean currents, and tidal variation. In the waters off the coast of New England, water temperature varies in the range 5° C. to 23° C. It is also well known that $CO_2$ solubility is affected by such temperature fluctuations [Markham, A. E., Kobe, K. A. £ *Am. Chem. Soc.* 1941, 63, 449].

While in a laboratory setting, temperature effects on sensor measurements may be reduced or eliminated completely by performing all experiments in a controlled temperature bath, for practical applications of sensor deployment, the effect of ambient temperature changes on sensor measurements must be understood to assess the reliability of in-situ sensor measurements.

Temperature changes can affect the sensor response in several ways. Firstly, temperature may affect the fluorescence and intensity of an indicator dye and, where ratiometric dyes such as c-SNAFL-1 are employed, temperature changes may affect the fluorescence differently at the two excitation wavelengths. For example, increasing temperature reduces the quantum efficiency of most molecules and could reduce the fluorescence intensity of one transition relative to the other. Secondly, temperature increases cause a decrease in $pK_{in}$ and at a given pH, the ratio increases with increasing temperature. Finally, the pH of the analyte solutions, such as the bicarbonate buffer solution used with $CO_2$ sensors, is temperature dependent with the pH decreasing with increasing temperature. The overall effect of temperature on the sensor response is thus a complex combination of multiple temperature-sensitive processes.

Using the fundamental thermodynamic relationships $\Delta G^0 = -RT \ln K$ and $\Delta G^0 = \Delta H^0 - T\Delta S^0$ it has been shown that for a system containing one indicator dye and one principal pH buffer [Morrison, T. J., Billett, F. *J. Chem. Soc.* (1952), 3819]:

$$\frac{d \log(I_B / I_A)}{d T^{-1}} = \frac{\Delta H^0_{buffer} - \Delta H^0_{ind}}{2.303R} \quad [10]$$

where $I_A$ and $I_B$ are the fluorescence intensities of the acid and base forms respectively. According to Equation 10 a plot of log $(I_A/I_B)$ vs $T^{-1}$ should yield a straight line of slope $(\Delta H^0_{buffer} - \Delta H^0_{in})/2.303$ R.

Figure 7:
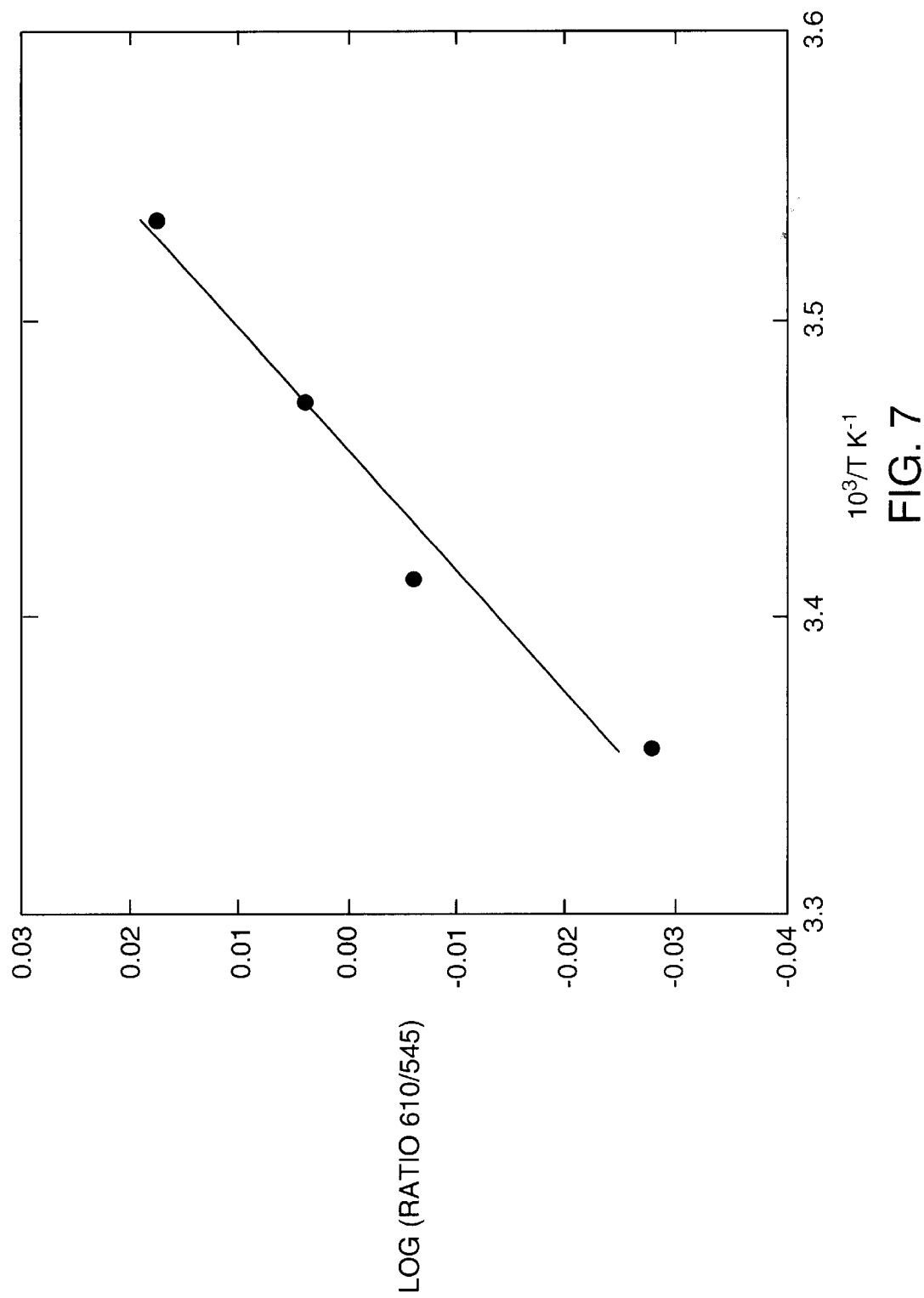
FIG. 7 is a plot showing the effect of temperature on the sensor response.

FIG. 7 shows a plot of $\log(I_A/I_B)$ vs $T^{-1}$, which, as predicted, yields a straight line. The measurement was performed at 12° C. in $N_2$ saturated solutions and the plot shows the corresponding log (Ratio 610 nm/545 nm) vs. 1/T according to Equation 10. These results suggest that for an accurate determination of $pCO_2$ an independent measurement of temperature must be made.

Field Test Evaluations

Oceanographic Monitoring of $pCO_2$ in Seawater:

There is clear evidence from environmental monitoring that a large proportion of the $CO_2$ produced by the burning of fossil fuels has a substantial, but not quantified, ocean sink. The extent to which this occurs and effects on the system brought about by climatic change are not fully understood [Merz, K. N 4. Jr., *J. Am. Chem. Soc.,* (1989), 111 (15), 5636]. This lack of understanding is due in part to the lack of extended time series data. The monitoring of $pCO_2$ in surface seawater has been achieved using titrimetry [Sarmiento, J. L., *US. JGOFS News,* (1995), 6(2), 4], coulometry [Dyrssen, D., *Ada Chemica Scand* (1965), 19, 1265], gas chromatography [Johnson, K. M., King, A. E., Sieburth, J. McN., *Marine Chem.* (1985), 16, 61], and IR spectrometry [Weiss, R. F., *J Chrom. Sc.* (1981), 19,611]. Although a number of fiber optic chemical sensors for seawater have been reported in the literature [Mills, A., Chang, Q. *Analyst,* 1993, 118, 839; Zhujun, Z., Seitz., W. R. *Anal. Chim. Acia.* 1984, 160, 305; Dickson, A. G. and Goyet, C. *Handbook of Methods for the Analysis of the Various Parameters of the Carbon Dioxide System in Sea Water* (1994), V.2, 5.1], most of these sensors do not exhibit the sensitivity required for monitoring the relatively small changes seen in ocean waters. As previously mentioned DeGrandpre, et al., have demonstrated an absorption-based fiber optic sensor system with excellent reported accuracy of ±2 ppm in the in the laboratory, but the system requires a fluid handling system which may not be appropriate for extended, autonomous operation [DeGrandpre, M. D., Hammar, T. R, Wallace, D. W. R, and Wirick, C. D., *Limn. Oceanogr.,* (1997), 42(1), 21].

Oceanographic Field Test Instrumentation:

For the remote sensor development and deployment, calibrations and other continuous on-line measurements were performed on a portable, hermetically-sealed fluorimeter, manufactured by Steve Brown Engineering (Livermore, Calif.), which was interfaced to an IBM-PC compatible computer. The sensor opto-electronic interface comprised the compact fluorimeter, a light emitting diode (LED) for excitation; dichroic and bandpass filters for separating and detecting the emitted light; and photodiode and lock-in amplifier detection electronics. This system was configured with a 485 nm with a 22 nm bandpass excitation filter (Omega, Brattleboro, Vt.), and the emission filters were 540 nm with a 30 nm bandpass and 630 nm with a 30 nm bandpass. The extended bandpass dichroic had a wavelength cutoff of 505 nm. The integration time for each measurement was 2 s. Data acquisition rate, filter switching, lamp and photodetector were software controlled by the computer.

The remote deployment system has low power consumption and is operated using a marine battery, recharged by solar panels, mounted next to the electronics. The portable fluorimeter was modified for at-sea tests by incorporation of an Onset Computer TT8 data logger and Persistor (Peripheral Issues) flashcard with extended memory. Power was provided by a marine battery recharged using two 1OW solar panels (Atlantic Solar Products). Line-of-sight communication was possible using a set of spread spectrum transceivers (Xetron Corp.) and data were telemetered using a SEIMAC PTT transmitter via the ARGOS satellite system.

Figure 11:
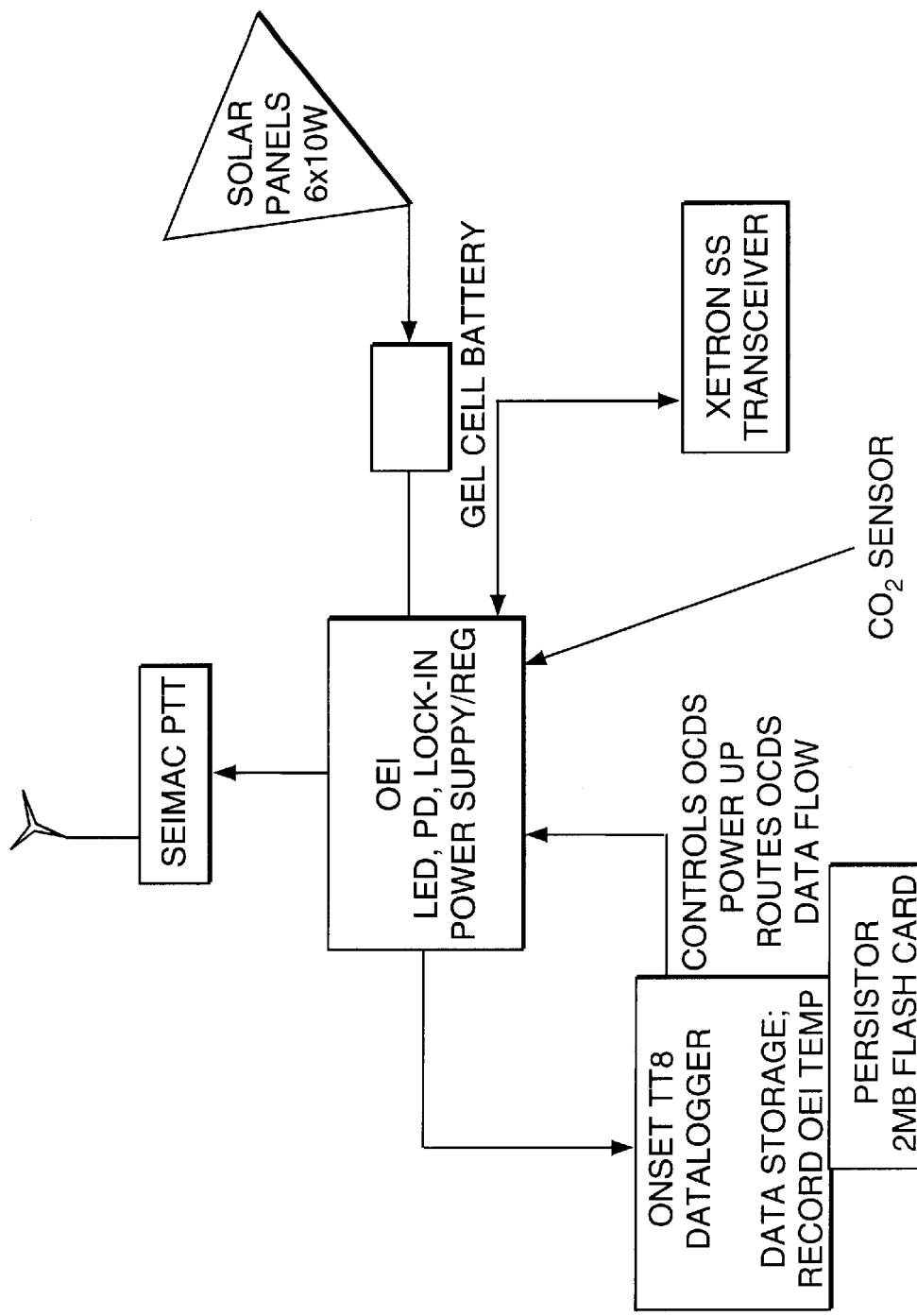
FIG. 11 shows a schematic block diagram of the overall $CO_2$ sensor system used in oceanographic monitoring of seawater.
Figure 12:
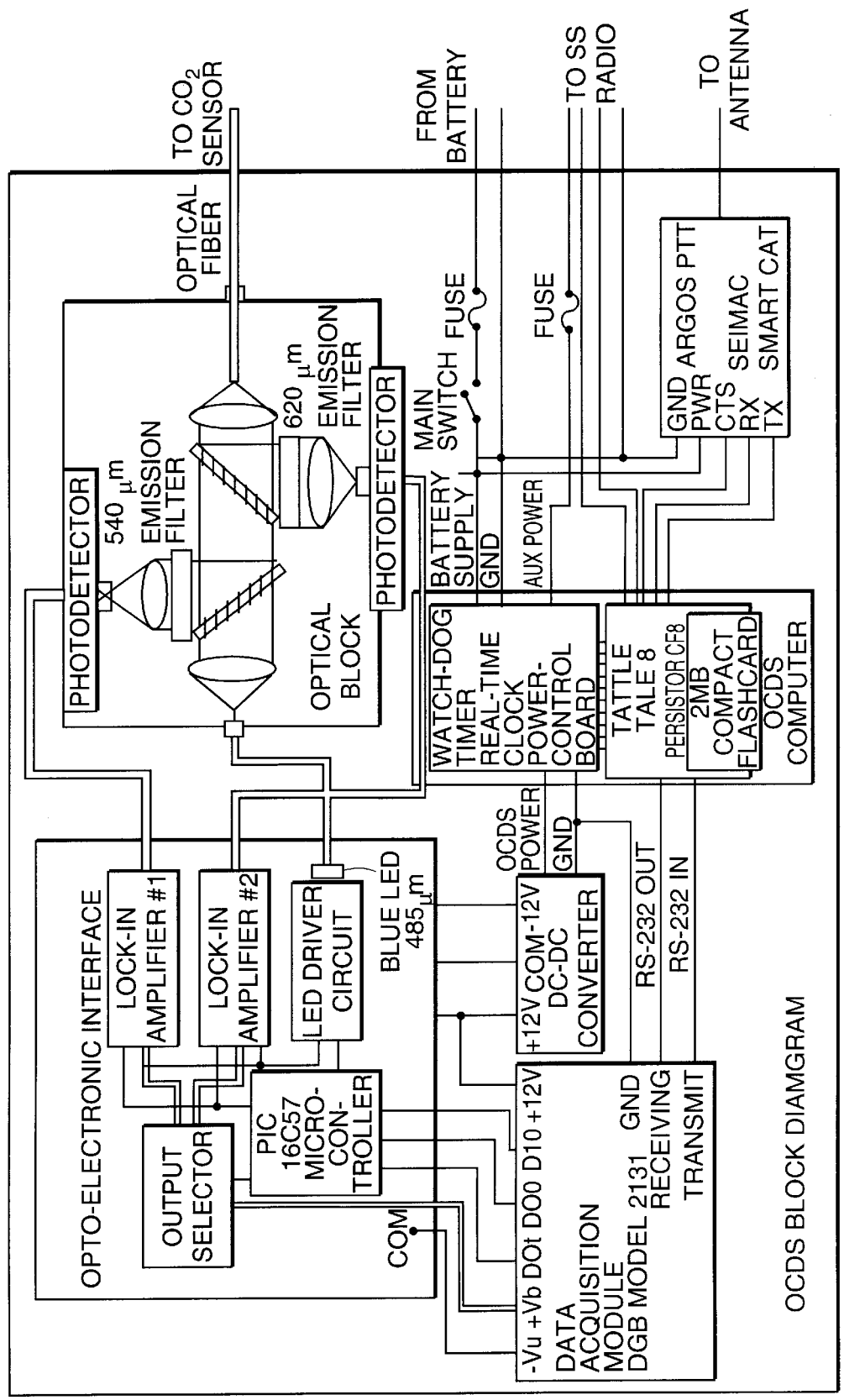
FIG. 12 is a schematic block diagram of individual system components used in oceanographic monitoring of $CO_2$.

Oceanographic Carbon Dioxide System (OCDS):

A schematic block diagram of the overall $CO_2$ sensor system used in oceanographic monitoring is shown inf FIG. 11. A block diagram of system components is shown in FIG. 12. A detailed description of the sensor system and its componenst is provided below.

OCEANOGRAPHIC CARBON DIOXIDE SYSTEM

The OCEANOGRAPHIC CARBON DIOXIDE SYSTEM (OCDS) consists of the following major components:

1. OCDS Computer
2. DC-DC Converter
3. Data Acquisition Module
4. Opto-Electronics Interface
5. Optical Block
6. OCDS Sensor
7. ARGOS PTT
8. Battery
9. Solar Power Regulator
10. Solar Panels
11. Spread-Spectrum Transceiver Each of these components will be described in detail in the following sections. The reader may refer to the OCDS Block Diagram to better understand the relationship of the components.

1. OCDS COMPUTER

The OCDS Computer controls the operation of the sensor electronics, records OCDS data, formats data for transfer to the ARGOS PTT and provides the user with a command-line interface for setup and control. The computer consists of several components:

Tattletale model S (TTS),
Persistor CFS,
2 MB CompactFlash_Card,
Battery-backed Real-Time Clock,
Power Control Board, and
Watch-Dog timer.

Tattletale model S

A Tattletale model S (ONSET Computer Corporation, Bourne, Mass.) single-board computer is employed. The TTS is a dual processor computer with a Motorola 68332 32-bit central processor and a PIC 16C64 slave processor and has the following specifications:

| RAM | 256 kilobytes | Data |
|---|---|---|
| EEPROM | 256 kilobytes | Program storage |
| Serial EEPROM | 8 kilobytes | Configuration parameters |
| A/D | 8 channels, 12 bits | |

For the OCDS, the TTS It is configured with three bi-directional asynchronous serial ports:

| 1 | User Interface port | 9600 baud |
|---|---|---|
| 2. | OCDS control/data port | 9600 baud |
| 3 | PTT data port | 4800 baud |

2. DC-DC CONVERTER

An isolated DC-DC converter (ACON Inc., South Easton Mass. model E15D2412) provides stable ±12 volts power to the OEI board and 12 volts to the DGH module. The input supply is connected to switched power channel 1 of the Power Control Board.

3. DATA ACQUISITION MODULE

A DGH Model 2131 (DGH Corporation, Manchester, N.H.) is employed to provide communications between the TTS and the PIC micro-controller on the OEI board. The TTS communicates with the DGH via RS-232 using ASCII commands. The DGH then communicates with the OEI PIC micro-controller using 2-wire clocked serial communications employing the DO0 and DO1 data lines. The DGH also provides a single 16-bit Analog to Digital converter which is used to read each of th two detector channels from the OEI board.

4. OPTO-ELECTRONICS INTERFACE (OEI)

The Opto-Electronics Interface (Lawrence Livermore National Laboratory, Livermore, Calif.) is a single 5×7 inch circuit board that provides the interface between the optical block and the data acquisition and control systems. The OEI generates the LED drive signal and processes the low-level analog signals from the photo-detectors using a lair of lock-in amplifiers. The operation of the OEI is controlled by an onboard PIC micro-controller.

Lock-in Amplifiers

A pair of Analog Devices (Norwood, Mass.) Model 630 Balanced Modulator-Demodulator chips are configured to operate as Lock-in amplifiers. A lock-in amplifier is essentially a synchronous demodulator followed by a low-pass filter. In this instance, lock-in amplification is employed to separate the small, narrow band photo-detector signal from the background noise. This allows these very small signals to be detected in the presence of uncorrelated noise since the frequency and phase of the signal are known.

Excitation LED Driver Circuit

The excitation LED circuit is controlled by the PIC micro-controller and enables the 30 kilohertz square wave output that drives the Blue LED. The LED is fitted with a 485 nm with 22 nm bandpass excitation filter. The driver frequency is connected to the two lock-in amplifiers to provide synchronizing signal to the lock-in amplifiers.

Micro-controller (MicroChip PIC 16C57)

The PIC micro-controller controls the operation of the OEI electronics and allows the gain and phase settings for each Lock-in amplifier to be controlled externally. Currently the PIC is configured so the phase is set by a DIP switch on the OEI board while the gain is controlled by the OCDS Computer.

Output Selector

The output selector is controller by the PIC controller and determines which analog is sent to the Data Acquisition Module. Commands relayed from the OCDS Computer via the Data Acquisition module were used to control the channel selector.

5. OPTICAL BLOCK

The Optical Block (Steve Brown Engineering, Livermore, Calif.) is essentially a two-channel fluorimeter and contains the following components:

Beam Splitter

A pair of dichroic mirrors arranged at 45 degrees to the light path allows the 485 nm excitation signal through the optical block, but to the split the returned signal before passing the signal through the emission filters.

Emission Filters

Two emission filters 540 nm and 620 nm each with a 30 nm bandpass are employed to separate the desired frequency bands from the incoming optical signal.

Photo-detector

Each photo-detector consists of a photodiode configured to operate n the photovoltaic mode, which produces excellent linearity but exhibits dark currents that increase in proportion to the bias voltage. A pair of series-connected AD745 op-amps provide pre-amplification.

6. OCDS SENSOR

The OCDS sensor is located at the distal end of a 12-foot section of 400-micron multi-mode optical fiber. Detail of the OCDS sensor are described above.

7. ARGOS PTT

A Smart-CAT Argos PTT (SEIMAC Ltd., Halifax, NS) is the primary data telemetry system. The PTT was ordered with the extended voltage option and two ARGOS IDs. The PTT is connected to serial port 3 on the Main Computer. The Clear-To-Send (CTS) line from the PTT is monitored by the Main Computer to determine when to transfer OCDS data to the PTT. The PTT is powered directly from the battery supply and will therefore continue to operate even if the Main Computer and OCDS suffer a complete failure.

8. BATTERY

A 12-volt 220 amp-hour type 27 Gel-Cell battery (Hamilton Ferris Corp., Ashland, Mass.) is the primary power source for the OCDS.

9. SOLAR POWER REGULATOR

A SunSaver-6 Photovoltaic System Controller (Morningstar Corporation, Olney, Md.) is used to interface the solar panel array to the battery. The SunSaver employs series Pulse Width Modulation (PWM) charge control which provides a constant voltage charging current.

10. SOLAR PANELS

Six MSX-10 (10 watt) photovoltaic panels (Solarex Corp., Gaithersburg, Md.) are fitted to charge the battery. The panels are mounted vertically on the superstructure of the ALTOMOOOR buoy. The positive terminal of each panel is connected to a Schottky diode.

11. SPREAD SPECTRUM RADIO TRANSCEIVER

A one-watt 928 MHz Spread-spectrum radio transceiver (XETRON Corp., Cincinnati Ohio) is connected to a main RS-232 port of the OCDS Computer and allows command and control of the OCDS from distances of up to 2 kilometer. The radio is mounted in a waterproof junction box bolted to the buoy superstructure. In order to conserve power, the radio transceiver in only powered for 5-minutes every half hour.

To allow for future expansion, four additional serial ports may be enabled to accommodate extra sensors and/or data telemetry devices.

For the OCDS application, the TTS is configured to operate at 8 MHz. All program control parameters and calibration coefficients are stored in the TTS EEPROM. The software is written in the C language and compiled for the TTS using the MetroWerks CodeWarrior C compiler with the MotoCross cross-compiler and stored on the FlashCard.

Persistor CFS

The Persistor CFS (Peripheral Issues, Mashpee Mass.) provides the interface between the TTS and the CompactFlash_. The PicoDOS_operating system allows the use of high-level function calls and the file system is fully DOS_compatible.

CompactFlash_card (2MB)

The OCDS data are stored in files stored on an industry 2MB CompactFlash_card (SanDisk Corporation). The CompactFlash is considered the most successful of the sub-PCMCIA sized recording media, specifically aimed at the digital camera and PDS markets.

Real-Time Clock

The Real-Time Clock (JAS Research Inc., Cambridge, Mass.) consists of a Motorola MC68HC68T1 Real-Time Clock chip with a 32.768 kilohertz SEIKO Temperature Controlled Oscillator (TCXO). The clock is powered from the OCDS Computer 5-volt logic bus with a 3 volt lithium battery backup. The clock chip is interfaced to the Tattletale S using clocked serial logic which provided high-speed read and write capability.

Power Control Board

The Power Control Board (JAS Research Inc., Cambridge, Mass.) provides three independently controlled FET (IRF-9530) power switches. One is dedicated to the Watch Dog Timer and the remaining two are under program control and are allocated as follows:

Channel 1 OCDS power control

Channel 2 Spread-spectrum radio power control

Watch Dog Timer

The watch-dog timer (JAS Research Inc., Cambridge, Mass.) is included to ensure that the OCDS continues to operate even if the software hangs-up or crashes. The timer is equipped with an independent time-base has a 10-minute time-out interval and is reset by the Tattletale 8 every minute. If it is not reset, the timer will remove power from the OCDS Computer for 3 seconds before re-applying the power.

OCDS MEASUREMENT CYCLE

The OCDS Computer is currently configured to take OCDS measurement every 30 minutes with measurements taken at 00 and 30 minute after each hour. The OCDS sensor package (DGH and OEI) is turned on by the OCDS Computer. However, when the OEI board is turned on, the default state of the LED driver is on. Therefore, the first task after the OCDS is powered and communication have been established is to turn off the LED driver. Once this is accomplished, readings on each channel are taken to measure the dark current from each photo-detector. The LED is then turned on and the measurements repeated for each channel. In each case five measurements are taken and averaged. The average dark current is then subtracted from the average signal. As soon as the measurements are completed the LED is turned off again. The intent is to minimize the amount of time the LED is on so as to minimize the bleaching effect light on the dye in the sensor. The data are then formatted for storage on the flash card. The following data are recorded in comma-delimited ASCII format for each measurement cycle:

julian_day, record_count,

Month,

Day,

Year,

Hour,

Minute,

Seconds,

DGH Status bit (0 or 1),

Average offset voltage channel 1,

Average offset voltage channel 2,

Average signal voltage channel 1,

Standard deviation signal voltage channel 1,

Average signal voltage channel 2,

Standard deviation signal voltage channel 2,

Ratio of channel 1 versus channel 2,

Temperature inside OCDS enclosure,

OCDS current drain,

Battery voltage.

Figure 9:
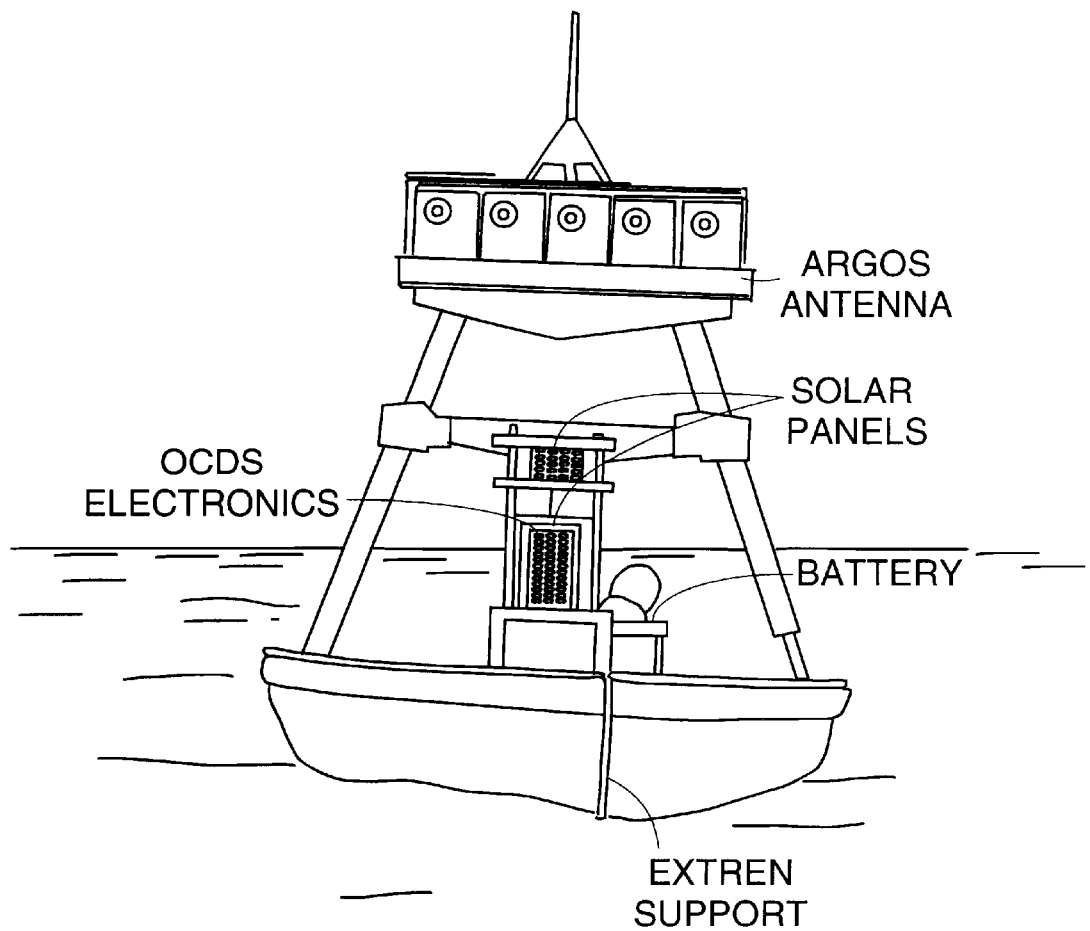
FIG. 9 is a schematic of the fiber optic $pCO_2$ sensor system deployed on a discus buoy in Vineyard Sound, Mass., approximately 0.3 km offshore, 41 deg, 31', 50"N, 70 deg, 38', 26"W.

Field Test Deployment and Measurements:

The integrated sensor system was deployed in the Atlantic Ocean on a discus-type offshore buoy located in Vineyard Sound, Woods Hole, Mass. FIG. 9 is a schematic of the fiber optic $pCO_2$ sensor system deployed on the discus buoy at a position approximately 0.3 km offshore, 41 deg, 31', 50"N, 70 deg, 38', 26"W; The fiber optic cable was guided through an Extren tube extending off the side of the buoy to provide a rigid support, and when in place, the sensor was approximately 2 m below the sea surface. A light baffle was installed at the end of this tube to eliminate intense scattered sunlight in the upper water column. A TT8 data logger is integrated into the instrument and used to control power up, timing, and data acquisition parameters. A Platform Transmitter Terminal (PTT) is integrated into the electronics and data are telemetered every 90 seconds via the ARGOS satellite system. This data transmission protocol allows data to be sent from the sensor system to a central station where it can be accessed via the Internet. There is approximately a 2–3 hour delay time between data transmission and availability of data to the user. Therefore, a spread spectrum transceiver set was installed and used for line-of-sight communication with the sensor system. The transceivers provide real-time, two-way communication with the system. This capability is particularly useful during emplacement on a buoy at sea using a ship or small craft, and permits verification of system status and adjustment of parameters such as gain, phase, and signal integration times prior to leaving the vicinity of the buoy.

Figure 10:
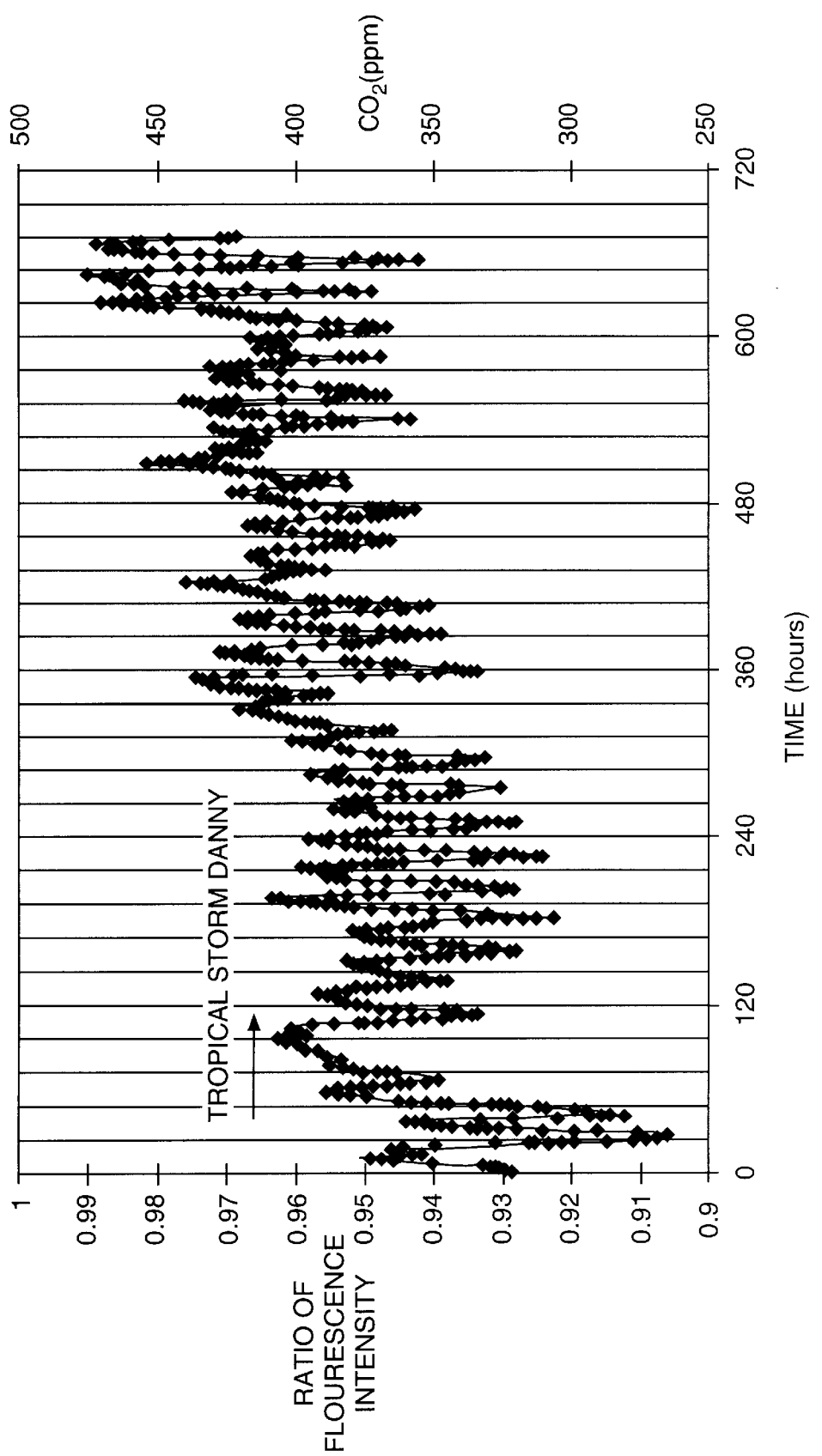
FIG. 10 is a plot of $pCO_2$ data collected from the sensor system of FIG. 9. Diurnal variations in $pCO_2$ are evident.

After extensive sensor characterization in the laboratory, the $CO_2$ measurement system was deployed for seawater $pCO_2$ monitoring for approximately seven weeks. A subset of the collected data is shown in FIG. 10, where the ratio, S1/S2, corresponding to the fluorescence intensity from the individual photodetector channels is plotted as a function of time. The measurement results shown in FIG. 10 suggests that the sensor is identifying diurnal variations in $pCO_2$ arising from both changes in surface seawater temperature and from biological activity. Based on laboratory sensor calibration the mean seawater $CO_2$ concentration was measured at 380 ppm during the first two weeks of the test. The apparent drift upwards in the signal ratio starting around hour 320 is likely related to microbial fouling which changes the $CO_2$ concentration in the microenvironment around the sensor. Observation of the sensor tubing after retrieval showed substantial fouling of the outer Extren guide tube and moderate fouling of the fiber cable and sensor housing.

In order to compare sensor measurements with conventional analytical results, water samples were taken periodically during the later two weeks of the sensor deployment. These samples were subsequently analyzed by conventional laboratory methods. Total alkalinity and total $CO_2$ were determined by potentiometric titration using a method derived from Dyrssen's method [Dyrssen, D., *Ada Chemica Scand* (1965), 19, 1265] as later modified by Bradshaw et al. [Bradshaw, A. L., Brewer, P. G., Shafer, D. K., and Williams, R. T., *Earth and Planetary Science Letters,* (1981), 55, 99]. The automated titration was performed in a closed cell maintained at constant temperature (25±1° C.). The ionic strength of the hydrochloric acid solution (0.IN) was adjusted with NaCl to better approximate seawater. The precision of the measurement is estimated to be better than 0.15%. The laboratory analyses provided a mean seawater $CO_2$ concentration of approximately 357 ppm for the later two weeks of the field test.

Test results from convention sampling and analysis methods were comparable to the fiber optic chemical sensor results obtained during the first two weeks of deployment and this field test demonstrated the feasibility of using a fiber optic chemical sensor and data acquisition system for remote, low-level, extended and unattended monitoring of pCO$_2$ in seawater. The fiber optic sensor was sufficiently robust to survive a range of weather and wave conditions after undergoing eight months of testing in a laboratory environment. Furthermore, the ability to telemeter data using the ARGOS satellite system and to control system parameters remotely demonstrated the unique capabilities and utility of the sensor and sensing system for long-term, remote deployment for environmental monitoring of low-level CO$_2$ by employing either a stationary buoy or a drifting, expendable buoy.

Additional Sensor Embodiments

Additional embodiments for improving sensor response time by the addition of enzymes, such as carbonic anhydrase, may provide improved temporal resolution for applications in a more dynamic environment such as coastal waters or tidal basins. The fiber optic system measurements may be further enhanced by incorporating real-time seawater temperature measurements and corrections for sensor response, providing temperature correction circuitry in the system electronics, and employing temperature correction algorithms to raw sensor data. Problems associated with microbial fouling may be addressed by application of anti-fouling paints or coatings or by employing controlled-release antifouling materials.

The present invention is not to be restricted in form nor limited in scope except by the claims appended here.

We claim:

1. A fiber optic chemical sensor for detecting a target analyte in a fluid sample comprising:
   at least one optical fiber;
   an optical interrogation zone disposed at a distal end of said fiber, said interrogation zone comprising an interrogated sample solution comprising a target analyte and an initial quantity of indicator dye, said interrogation zone being optically coupled to and in optical communication with said fiber; and
   a dye reservoir comprising excess indicator dye solution, said reservoir being in fluid contact with said interrogation zone so as to permit fluid transport of said excess dye between said reservoir and said interrogation zone sample solution, while said dye reservoir is optically isolated from said interrogation zone.

2. The sensor of claim 1 wherein said dye reservoir further comprises a fluid chamber formed by a sensor housing, said excess dye being confined in said chamber.

3. The sensor of claim 1 wherein said dye reservoir further comprises a dye support material positioned within a sensor housing, said excess dye being mobile and fluidly transportable within said support material.

4. The sensor of claim 3 where said dye support material is selected from the group consisting of poly-N-vinylpyrrolidone, polytetrafluoroethylene, polyacrylamide, polyhydroxethylmethacrylate, celluloase nitrate, polysulfones, polycarbonates, polyurethanes, nylons and polyethylende glycols.

5. The sensor of claim 1 wherein said dye reservoir further comprises:
   a fluid chamber formed by a sensor housing, said excess dye being confined in said chamber; and
   a dye support material positioned within said fluid chamber, said excess dye being mobile and fluidly transportable with said support material.

6. The sensor of claim 4 where said dye support material is selected from the group consisting of poly-N-vinylpyrrolidone, polytetrafluoroethylene, polyacrylamide, polyhydroxethylmethacrylate, celluloase nitrate, polysulfones, polycarbonates, polyurethanes, nylons and polyethylende glycols.

7. The sensor of claim 1 further comprising an analyte permeable membrane covering a portion of said sensor surface, said membrane disposed between said sensor and said fluid sample, said membrane providing for transport of a target analyte in said sample to said optical interrogation zone, said membrane restricting transport of said indicator dye between said interrogation zone and said sample.

8. The sensor of claim 7 wherein said membrane is selected from the group of gas permeable materials consisting of silicones, polytetrafluorethylene, cellulose nitrate, polyethylene, polyvinyl chloride, polyvinylidene chloride, polysulfones, polycarbonates, polyurethanes, polyhydroxymethlmethacrylate, nylons and polyethylene glycols.

9. The sensor of claim 1 further comprising a light source.

10. The sensor of claim 1 further comprising a light detector.

11. A method of making a fiber optic sensor comprising:
    providing at least one optical fiber;
    incorporating an optical interrogation zone at a distal end of said fiber, said interrogation zone comprising an interrogated sample solution comprising a target analyte and an initial quantity of indicator dye, said interrogation zone being optically coupled to and in optical communication with said fiber; and
    forming a dye reservoir comprising excess indicator dye solution, said reservoir being in fluid contact with said interrogation zone so as to permit fluid transport of said excess dye between said reservoir and said interrogation zone sample solution, while said dye reservoir is optically isolated from said interrogation zone.

12. The method of claim 11 further comprising the step of:
    covering a portion of said sensor surface with and analyte permeable membrane, said membrane providing for transport of a target analyte in a sample fluid to said interrogation zone, said membrane restricting transport of said indicator dye between said interrogation zone and said sample fluid.

13. A method for determining the concentration of a target analyte in a fluid sample comprising the steps of:
    providing at least one optical fiber comprising
        an optical interrogation zone at a distal end of said fiber, said interrogation zone comprising an interrogated sample solution comprising a target analyte and an initial quantity of indicator dye, said interrogation zone being optically coupled to and in optical communication with said fiber; and
    a dye reservoir comprising excess indicator dye solution, said reservoir being in fluid contact with said interrogation zone so as to permit fluid transport of said excess dye between said reservoir and said interrogation zone sample solution, while said dye reservoir is optically isolated from said interrogation zone;
    contacting said distal end of said fiber with said sample; and
    determining the concentration of said analyte.

14. The method of claim 13 wherein said providing further comprises covering a portion of said sensor surface with and analyte permeable membrane, said membrane providing for transport of a target analyte in a sample fluid to said interrogation zone, said membrane restricting transport of said indicator dye between said interrogation zone and said sample fluid.

* * * * *

UNITED STATES PATENT AND TRADEMARK OFFICE
CERTIFICATE OF CORRECTION

PATENT NO. : 6,285,807 B1
DATED : September 4, 2001
INVENTOR(S) : David R. Walt et al.

It is certified that error appears in the above-identified patent and that said Letters Patent is hereby corrected as shown below:

Column 1,
Line 3, after the title and before the "FIELD OF THE INVENTION", please add the following:

-- GOVERNMENT SUPPORT

This invention was supported by OCE-9102670 awarded by the National Science Foundation. The government has certain rights in the invention. --

Signed and Sealed this

Fifth Day of April, 2005

JON W. DUDAS
*Director of the United States Patent and Trademark Office*